(12) United States Patent
Mains, Jr.

(10) Patent No.: US 11,406,708 B2
(45) Date of Patent: *Aug. 9, 2022

(54) METHODS, APPARATUSES, AND SYSTEMS FOR TRACKING FREIGHT

(71) Applicant: CRC R&D, LLC, Kenner, LA (US)

(72) Inventor: Ronald H. Mains, Jr., Kenner, LA (US)

(73) Assignee: CRC R&D, LLC, Kenner, LA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/170,587

(22) Filed: Feb. 8, 2021

(65) Prior Publication Data

US 2021/0154293 A1 May 27, 2021

Related U.S. Application Data

(63) Continuation of application No. 15/519,549, filed as application No. PCT/US2015/055741 on Oct. 15, (Continued)

(51) Int. Cl.
*A61K 39/39* (2006.01)
*A61K 39/395* (2006.01)
(Continued)

(52) U.S. Cl.
CPC .... *A61K 39/3955* (2013.01); *C07K 14/70578* (2013.01); *C07K 16/2875* (2013.01);
(Continued)

(58) Field of Classification Search
CPC .................................................. A61K 39/3955
See application file for complete search history.

(56) References Cited

U.S. PATENT DOCUMENTS 5,712,789 A * 1/1998 Radican ............. G06Q 10/0875
705/28
6,556,138 B1 * 4/2003 Sliva ..................... B65F 1/1484
340/568.1

(Continued)

FOREIGN PATENT DOCUMENTS

WO 2006084255 8/2006

OTHER PUBLICATIONS

ITS International, Savings accrue from on-line from truck Screening, Dec. 8, 2013, https://web.archive.org/web/20131208174419/ https://www.itsinternational.com/sections/cost-benefit-analysis/features/savings-accrue-from-on-line-from-truck-screening/ (Year: 2013).

(Continued)

*Primary Examiner* — Travis R Hunnings
(74) *Attorney, Agent, or Firm* — Jason P. Mueller; FisherBroyles, LLP

(57) ABSTRACT

Methods, apparatus, and systems are provided for tracking freight. Embodiments include a tracking device for a trailer containing a load. The tracking device may include a housing including a connector, a main body, and a GPS tracker located within the main body and configured to track the location of the load. Tracking device may include a support member linking the connector and main body. Connector may securely attach to a container on the trailer and attach to a seal such that the container cannot be opened without breaking the seal. Support member may stabilize the housing and protect the tracking device during transit of the load. A tracking system may implement to monitor, gather information and report on the tracking device and the load.

19 Claims, 20 Drawing Sheets

Related U.S. Application Data 2015, now Pat. No. 10,912,829, which is a continuation of application No. 14/521,361, filed on Oct. 22, 2014, now Pat. No. 10,019,878.

(60) Provisional application No. 62/064,331, filed on Oct. 15, 2014.

(51) Int. Cl.

| | | |
|---|---|---|
| *H04W 4/029* | (2018.01) | |
| *G06Q 10/08* | (2012.01) | |
| *G08B 13/24* | (2006.01) | |
| *C07K 14/705* | (2006.01) | |
| *C07K 16/28* | (2006.01) | |
| *A61K 38/00* | (2006.01) | |
| *A61K 39/00* | (2006.01) | |

(52) U.S. Cl.
CPC ......... *G06Q 10/08* (2013.01); *G06Q 10/0833* (2013.01); *G08B 13/2434* (2013.01); *G08B 13/2462* (2013.01); *H04W 4/029* (2018.02); *A61K 38/00* (2013.01); *A61K 2039/505* (2013.01); *C07K 2317/52* (2013.01); *C07K 2319/30* (2013.01)

(56) References Cited

U.S. PATENT DOCUMENTS

| | | | |
|---|---|---|---|
| 7,312,702 B1* | 12/2007 | Willms | G06Q 50/26 |
| | | | 705/333 |
| 8,219,503 B2* | 7/2012 | Takahashi | G06Q 10/0833 |
| | | | 705/26.1 |
| 8,279,067 B2* | 10/2012 | Berger | G06Q 10/08 |
| | | | 340/572.8 |
| 10,019,878 B2* | 7/2018 | Mains, Jr. | C07K 16/2875 |
| 10,127,556 B2 | 11/2018 | Lesesky | |
| 10,293,842 B2 | 5/2019 | Miyajima | |
| 10,388,162 B2 | 8/2019 | De Moura | |
| 10,769,947 B2 | 9/2020 | De Moura | |
| 10,772,957 B2* | 9/2020 | Mains, Jr. | A61K 39/3955 |
| 10,912,829 B2* | 2/2021 | Mains | G06Q 10/0833 |
| 10,990,109 B2 | 4/2021 | Nelson | |
| 2003/0063000 A1 | 4/2003 | Grimm | |
| 2004/0155778 A1* | 8/2004 | Shek | G06K 19/07758 |
| | | | 340/572.1 |
| 2005/0071247 A1 | 3/2005 | Kelley | |
| 2005/0116833 A1 | 6/2005 | Miller | |
| 2005/0231365 A1* | 10/2005 | Tester | G09F 3/0347 |
| | | | 292/307 R |
| 2006/0109106 A1 | 5/2006 | Braun | |
| 2007/0083600 A1 | 4/2007 | Bakos | |
| 2009/0032510 A1 | 2/2009 | Ando | |
| 2009/0265223 A1* | 10/2009 | Takahashi | G06Q 30/0601 |
| | | | 705/26.1 |
| 2009/0322510 A1* | 12/2009 | Berger | G06Q 10/08 |
| | | | 340/568.1 |
| 2011/0128143 A1* | 6/2011 | Daniel | G08B 21/0261 |
| | | | 455/12.1 |
| 2011/0133888 A1* | 6/2011 | Stevens | G06Q 50/28 |
| | | | 340/8.1 |
| 2011/0133932 A1* | 6/2011 | Tan | G09F 3/0376 |
| | | | 340/568.1 |
| 2012/0002045 A1 | 1/2012 | Tony | |
| 2013/0016636 A1 | 1/2013 | Berger | |
| 2014/0006302 A1 | 1/2014 | Mcquillan | |
| 2014/0067313 A1 | 3/2014 | Breed | |
| 2014/0074257 A1 | 3/2014 | Bhargava | |
| 2014/0218218 A1 | 8/2014 | Lloreda | |
| 2014/0306833 A1 | 10/2014 | Ricci | |
| 2014/0309789 A1 | 10/2014 | Ricci | |
| 2015/0081582 A1 | 3/2015 | Mains, Jr. | |
| 2018/0211534 A1 | 7/2018 | De Moura | |
| 2018/0268379 A1 | 9/2018 | Collins | |
| 2018/0305876 A1 | 10/2018 | Langford | |
| 2019/0035274 A1 | 1/2019 | Sabagh | |

OTHER PUBLICATIONS

"Big Bend Travel Plaza: Driver Services", published by wwww.bigbendtravelplaza.com on Jan. 8, 2011 (Year: 2011).
"Hotel internet services", published by www.hotelwifi.com, in 2012 (Year: 2012).
USPS Yard Management System—VOA Manual WhereNet, Accenture, Apr. 23, 2012 (Year: 2012).
C3 Yard datasheet C3 Solutions, Inc., 2016 (Year: 2016).
C3 Solutions Case Study—UK Parcel Delivery Company C3 Solutions, Inc. 2016 (Year: 2016).
The Synchronized Distribution Supply Chain—Best Practices in Yard Management Motorola, 2013 (Year: 2013).
Yard Smart—datasheet C3 Solutions Inc., 2013 (Year: 2013).
4Sight helps facilities capitalize on productivity using real-time data Plant Engineering, Jan. 18, 2011 (Year: 2011).
Braun, Gregory, A Practical Guide—Everything you need to know about buying a Dock Appointment Scheduling System C3 Solutions, May 2017 (Year: 2017).

\* cited by examiner

FastTrack

Dashboard | Home / Reports

Search

Reports

▦ Customer A

| Customer ▲ | BOL | Origin | Destination | Appointment Time | ETA | Status |
|---|---|---|---|---|---|---|
| Customer A | 10000 | Geismar, LA | Decatur, TX | 9/25/2014 3:42:49 PM | 9/26/2014 6:19:40 PM | Late |
| Customer A | 10001 | Geismar, LA | Decatur, TX | 9/25/2014 11:48:21 AM | 9/26/2014 6:32:00 AM | Late |
| Customer A | 10002 | Geismar, LA | Decatur, TX | 9/25/2014 7:00:02 PM | 9/26/2014 11:47:44 AM | Late |
| Customer A | 10003 | Geismar, LA | Decatur, TX | 9/27/2014 4:21:16 AM | 9/26/2014 8:31:33 AM | On Time |
| Customer A | 10004 | Geismar, LA | Decatur, TX | 9/25/2014 4:07:07 PM | 9/26/2014 8:55:19 AM | Late |
| Customer A | 10005 | Geismar, LA | Decatur, TX | 9/27/2014 8:36:10 AM | 9/26/2014 3:17:32 PM | On Time |
| Customer A | 10006 | Geismar, LA | Decatur, TX | 9/26/2014 5:49:16 AM | 9/26/2014 9:55:38 PM | On Time |
| Customer A | 10007 | Geismar, LA | Decatur, TX | 9/25/2014 5:48:51 PM | 9/26/2014 10:03:47 AM | Late |
| Customer A | 10008 | Geismar, LA | Decatur, TX | 9/25/2014 2:03:22 PM | 9/26/2014 2:43:25 PM | Late |
| Customer A | 10009 | Geismar, LA | Decatur, TX | 9/27/2014 12:02:16 AM | 9/26/2014 8:42:02 PM | On Time |

Showing 1 to 10 of 10 entries

Previous | 1 | Next

▦ Customer B

FIG. 5

| FastTrack | | | | | | | | | | | |
|---|---|---|---|---|---|---|---|---|---|---|---|
| 🏠 Dashboard | Home / Admin | | | | | | | | | | |
| 🛠 Admin | Shipments | | | | | | | | | □ — ⬚ ✕ | |
| 🔍 Search | 🔍 | | | | | | | | | 10 ▾ | |
| 📊 Reports | ID ▲ | Bill of Lading ◊ | Customer ◊ | Origin Street ◊ | Origin City ◊ | Origin State ◊ | Origin Zip ◊ | Destination ◊ | Destination Street ◊ | Destination City ◊ | Destination State ◊ | Destination Zip ◊ |
| | 1 | CRC 1234 | Cross road Centres | CRC | 32 E. Airline HWY. | Kenner | LA | 70062 | GB | 1106 Laguna Lane | Gulf Breeze | FL | 32563 |
| | Showing 1 to 1 of 1 entries | | | | | | | | | Previous 1 Next | |
| | Add a new shipment | | | | | | | | | | |

FIG. 6

METHODS, APPARATUSES, AND SYSTEMS FOR TRACKING FREIGHT

CROSS-REFERENCE TO RELATED APPLICATIONS

The present invention is a continuation of U.S. Nonprovisional application Ser. No. 15/519,549, filed Apr. 16, 2017, which is a National Stage of International Application No. PCT/US15/55741, filed Oct. 15, 2015, which is a continuation of U.S. Nonprovisional application Ser. No. 14/521,361, filed Oct. 22, 2014, which claims the benefit of U.S. Provisional Patent Application No. 62/064,331, filed Oct. 15, 2014, all of which are incorporated herein in their entirety by reference thereto.

FIELD

The present invention relates to methods, apparatuses, and systems for the tracking of freight, and in particular though non-limiting embodiments, to methods, apparatus, and systems for tracking freight sealed to trucks and containers by Global Positioning Systems ("GPS") via wireless communication.

BACKGROUND

GPS systems and mobile tracking applications are used to track freight in the transportation industry. Many existing systems, however, are prone to error for various reasons. Common problems include: durability and operability under adverse conditions; functionality in directly tracking a container containing cargo; and security. Regarding durability and operability, existing systems have typically not included housings capable of withstanding the swaying, bumps, wind, weather and other adverse conditions often encountered during truck transport. Regarding functionality, existing systems may provide incorrect information as to location of the actual load being transported because they are connected to the tractor and/or driver, not to the actual container housing the cargo. Indeed, it is not uncommon for existing systems to be hard-wired to freight hauling tractors and/or linked to a driver's cell phone, as opposed to being hard-wired to the actual freight. Regarding security, existing systems are not durable and may be easily tampered with. Further, the systems are typically not integrated with existing security systems for the container housing the cargo.

Accordingly, a need exists for methods, apparatuses, and systems for tracking freight having improved durability, functionality, and security.

SUMMARY

Embodiments of the present invention address the problems described above with respect to existing GPS receiver systems and mobile tracking applications that have been used to track freight in the transportation industry. Indeed, the present invention provides for new and improved methods, apparatuses and systems for tracking freight.

In an example embodiment of the present invention, a system is provided. The system includes a removable tracking device, a seal, and a container. The tracking device may be securely attached to at least one of the seal and the container such that the container cannot be accessed without breaking the seal. The system may include a bill of lading, the bill of lading not accessible without breaking the seal. The tracking device may include a rigid member with a connection at one end of the tracking device that connects the tracking device to at least one of the seal and the container. The rigid member may be an elongated member. A first end of the elongated member may be attached to a housing and a second end of the elongated member may be attached to at least one of the seal and the container such that the container cannot be accessed without breaking the seal. The tracking device may include a sensor that detects seal breakage and sends out a signal alert notifying of the breakage. The elongated member and the connection may be configured to securely attach the tracking device to the container and the seal to minimize movement and absorb loading while the container is being transported by a vehicle. The tracking device may include a universal connection adaptable for connection to multiple different types of seals and containers. The tracking device may weigh less than 10 pounds. The tracking device may include an accelerometer configured to measure the acceleration of the container, a GPS tracker configured to track the location of the container, a GSM communication configured to forward the acceleration and location of the container to a computer, and a power supply to provide power to the device. The sensor may be connected to a GSM communication in the tracking device. The tracking device may include a satellite communication apparatus configured to forward the acceleration and location of the container to a computer if GSM communication is not possible. The tracking device may include temperature and vibration sensors.

In another example embodiment of the present invention, a system for broker trucking is provided. The system includes at least one container having a load, a removable tracking device attached to the at least one container, a computer, and a user interface. The tracking device may be configured to continuously transmit a location of the at least one container. The at least one container may be sealed with a seal to prevent access to the load and tracking device without breaking the seal. The computer may be configured to continuously receive the location of the at least one container from the removable tracking device. The user interface may be configured to display the transmitted location of the at least one container as received by the computer to an administrator. The system may include a terminal at a warehouse. Warehouse personnel may input and transmit information to the computer notifying that the container has been loaded and that the device is ready to transmit the location of the container. The administrator may be located at the user interface and configured to use information regarding the location of the container to update arrival information. The location of the at least one container may be transmitted over GSM and the internet to the computer configured to receive the transmitted location. The location of the at least one container may be transmitted over satellite and the internet to the computer configured to receive the transmitted location. The computer may be interconnected with a Transportation Management System.

In an example embodiment of the present invention, a method of broker trucking is provided. The method may include the following steps: obtaining a tracking device and a bill of lading for a load; loading a container, connected to a trailer, with the load; sealing the container such that neither the load, tracking device or bill of lading can be accessed without breaking a seal; monitoring the container while the load is in transit; breaking the seal upon arrival of the container at a place of load delivery; removing the load from the container; and returning the tracking device and the bill of lading to a depository. The method includes inputting into a computer system that the container has been sealed and is ready to depart; and inputting into a computer system that the container has arrived. Inputting sealing and departure information may activate the tracking device and inputting arrival information may deactivate the tracking device.

In an example embodiment of the present invention, a tracking device for a trailer containing a load is provided. The tracking device includes a housing having a support member, a connector, and a main body. The main body may enclose a GPS tracker configured to track the location of the load. The connector may be connected to the support member. The support member may be connected to the main body, and the GPS tracker may be located within the main body. The connector may be configured to securely attach to a container on the trailer and to a seal such that the container cannot be opened without breaking the seal. The support member may be configured to stabilize the main body and protect the tracking device during transit of the load. The tracking device may include a sensor that monitors breakage of the seal, the sensor connected to a GSM communication device. The tracking device may include a satellite communication device configured to forward acceleration and location information of the container to a computer if GSM communication is not possible.

In an example embodiment of the present invention, a tracking device for a trailer containing a load is provided. The tracking device includes a housing including a connector and a main body. The main body may enclose a GPS tracker configured to track the location of the load. The connector may be connected to the main body and the GPS tracker may be located within the main body. The connector may be configured to securely attach to a container on the trailer and to a seal such that the container cannot be opened without breaking the seal. The tracking device may include a sensor that monitors breakage of the seal, the sensor connected to a GSM communication device. The tracking device may include a satellite communication device configured to forward acceleration and location information of the container to a computer if GSM communication is not possible. The connector may include an aperture for attaching and securing the connector to the seal. The aperture may have at least one of a substantially rectangular or circular shape. The connector may be configured for locking within at least one of bolt seals and wire seals. The housing may be at least one of a plastic and hybrid metal-plastic unit. The tracking device may be charged via at least one of a battery, supercapacitor, and wireless charging. The tracking device may be charged via magnetic induction utilizing a coil of wire and magnets placed within or around the housing.

DESCRIPTION OF DRAWINGS

FIG. 5 is a smart search screen of a tracking system with advanced textual reporting, according to an exemplary embodiment of the present invention.

FIG. 6 is an administration screen of a tracking system, according to an exemplary embodiment of the present invention.

DESCRIPTION

The present invention provides methods, apparatuses, and systems for tracking of freight, including methods, apparatuses, and systems for tracking freight sealed to trucks and containers by GPS via wireless communication.

According to an example embodiment of the present invention, a truck pulls up to a warehouse. Personnel greet the driver and load a trailer with appropriate freight and provide a bill of lading to the driver. After closing the trailer and/or container loading door(s), the personnel lock the load with a tracking device such that the tracking device is secured to the door(s) and a seal. The tracking device cannot be removed, or the door(s) opened, without breaking the seal. With the trailer loaded, secured and ready to depart, personnel approach a local terminal notifying a tracking system that the load is ready to depart or has departed. The tracking system processes the notification and initiates freight load tracking. The tracking system gathers information during transit of the load and processes the information for use by administrators. The administrators may monitor the load, and also update arrival times, connection times, as well as customers as to the status of the load. Once the load arrives at its destination, personnel break the seal, unload the trailer or container, and update the tracking system accordingly. The destination warehouse then forwards the tracking device to an appropriate location.

In various embodiments, the tracking system may include a container/trailer and tracking device configured to securely and universally integrate with existing load seals. The tracking device may house electronic circuitry and microcontrollers (mainboard, accelerometer, GPS tracker, GSM communication (Global System for Mobile Communications), power supply, satellite communication, optional additional sensors—e.g. temperature, vibration, and seal) and interface with a tracking system that may be web based. The tracking device electronic circuit board(s) may collect/transmit acceleration and GPS data to a web application via GSM and/or satellite communication. A physical or web-based service may facilitate connection between the tracking device and the web application. The tracking device and/or tracking system may provide an administrator with tracking data which may be utilized for various purposes, including administration, advanced reporting, and smart searching. This data may be automatically or manually entered into an existing company Transportation Management System (TMS).

Figure 1:
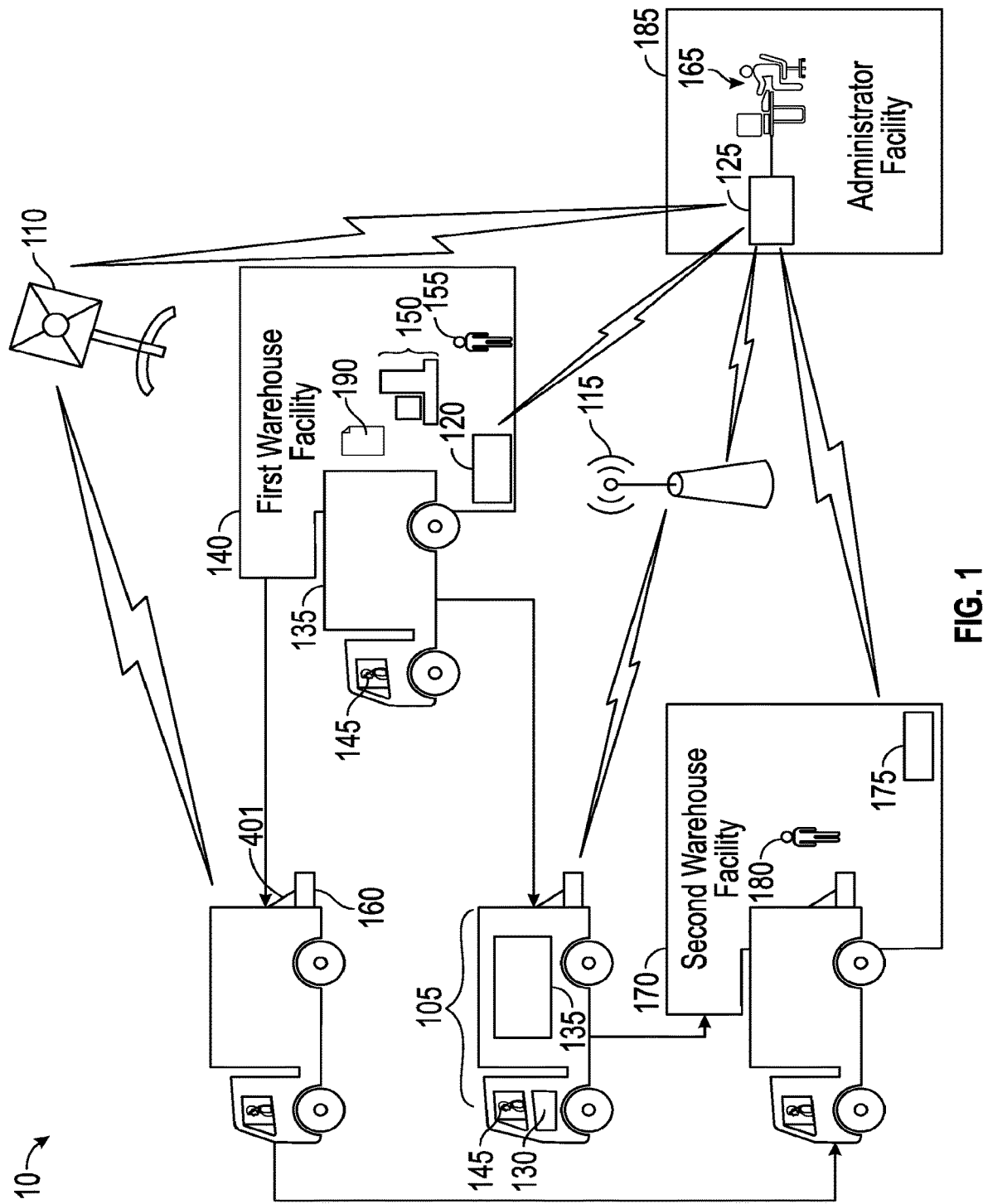
FIG. 1 is a schematic overview of a freight tracking system, according to an exemplary embodiment of the present invention.

FIG. 1 schematically depicts a tracking system (10) including warehouses (140, 170), a bill of lading (190), a container (135), bolt seal (401), and a tracking device (160). In various embodiments of the present invention, the system (10) may include greater or fewer components. At a first warehouse facility (140), a bill of lading (190) is given to driver (145) and load (150) is loaded into a trailer (105) (or a container (135) located in the trailer (105)) by warehouse personnel (155). Tracking device (160) is attached to trailer/container (105, 135) and then a seal (401) is used to secure the load (150). In one embodiment, the trailer/container (105, 135) may include doors that are latched together with overlapping flanges that include a central hole. Tracking device (160) includes a connector that attaches to the overlapping flanges of the doors and includes an aperture that aligns with the central hole of the doors. Seal (401) may be a bolt seal (401) that passes through the hole in the door flanges and the aperture in tracking device (160). An end piece is then placed on the seal (401) such that the doors, tracking device (160), and seal (401) are secured together. The doors cannot be opened and the tracking device (160) cannot be removed and/or tampered with without breaking the seal (401). Warehouse personnel (155) may then input into a local terminal (120) that the load (150) is ready to leave the warehouse (140), thereby activating tracking via the tracking system (10). Trailer/container (105, 135) departs the first warehouse (140) and while in transit continuously informs the tracking system computer (125) and/or administrator (165) of the trailer/container's (105, 135) position via GSM (115) and/or satellite (110). Once the trailer/container (105, 135) arrives at a second warehouse facility (170), warehouse personnel (180) unload the load (150). After unloading, personnel update a local terminal (175), thereby deactivating tracking system (10) tracking by the tracking system computer (125).

System (10) of the present disclosure may include a first (140), second (170), or further plurality of warehouse facilities. Furthermore, the warehouse facilities are not limited to enclosed truck freight logistic centers but may include docks, ships, or other facilities where efficient routing of cargo/freight is advantageous.

Bill of lading (190) of the present disclosure may take physical or digital forms documenting the cargo/load (150) while giving title to a specified party (e.g. delivery warehouse operator). Bill of lading (190) may be stored at various warehouse facilities and/or digitally within the tracking device (160) itself.

Trailer/container (105, 135) of the present disclosure may vary based on different embodiments. In some instances, a container (135) is attached to a trailer (105) and pulled by a tractor. In other instances, the container (135) is part of the trailer (105) and is pulled by a tractor. In other instances, the tractor, trailer (105), and container (135) are one unit. In other instances, the container (135) may be a shipping container, smaller container or the like that may be loaded on ships or other forms of transport such as cargo planes and helicopters.

Local warehouse terminals (120, 175) of the tracking system may comprise an additional desktop computer, iPad, and/or other network device that is capable of interacting with the tracking system computer (125). Terminals (120, 175) may be used to activate tracking by the tracking device (160) by warehouse personnel (155, 180). In other embodiments, the tracking system (10) may continuously and/or automatically track the tracking device (160).

Figure 1A:
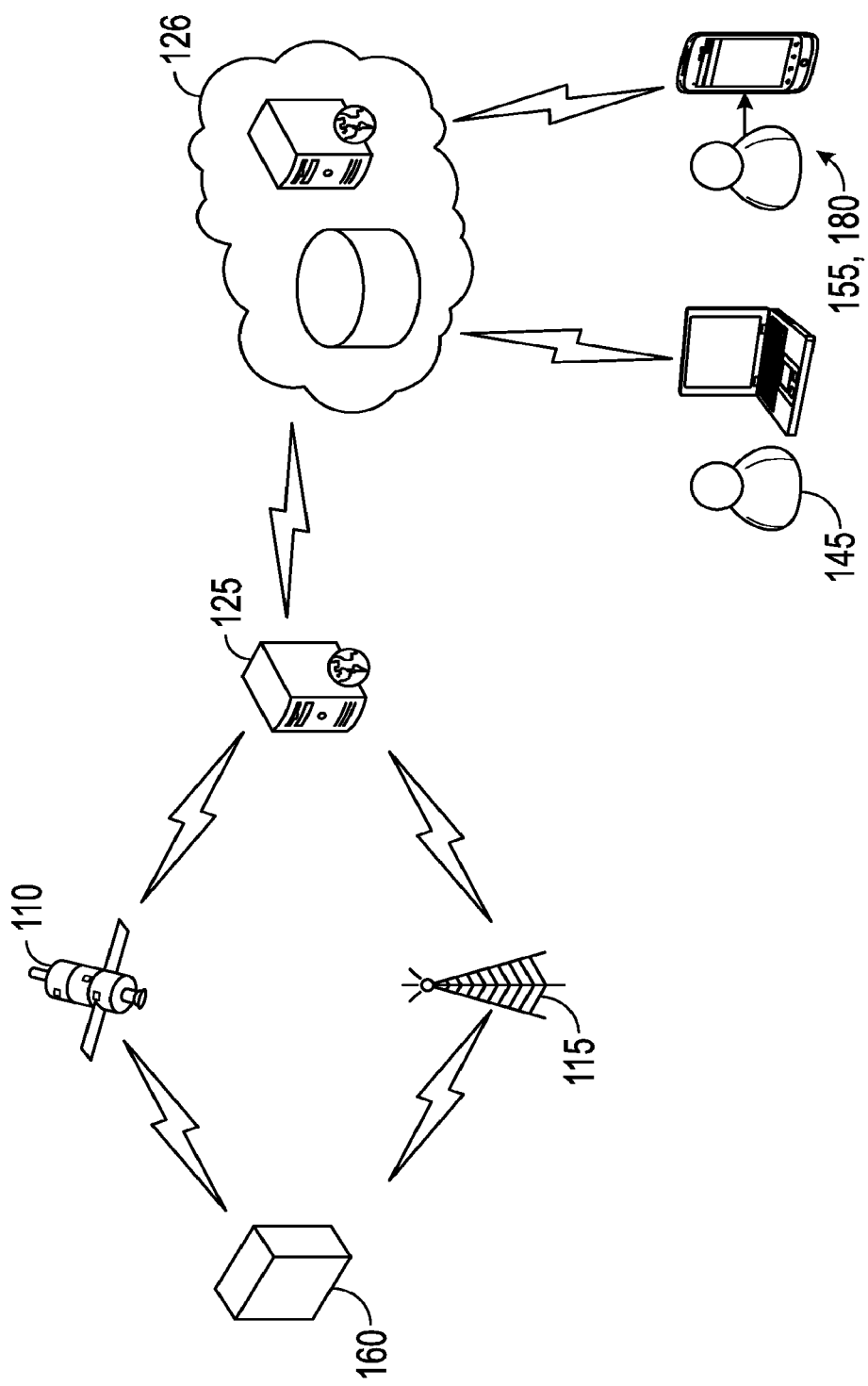
FIG. 1A is a schematic overview of an embodiment of the freight tracking system shown in FIG. 1.

In an exemplary embodiment, as shown in FIG. 1A, the tracking device (160) collects tracking information, including, for e.g., location data, which it then communicates to a customized web application/database (126) via computer (125). Web application/database (126) may then communicate this tracking information to a driver/user (145) and/or warehouse personnel (155, 180). Computer (125) of the tracking system (10) may encompass any suitable processing device connected to the tracking device (160). Computer (125) may be physical or web based (e.g. Amazon Web Services). Indeed, the computer (125) may be adapted to execute any operating system including Linux™ UNIX™ Windows™, or any other suitable operating system. In some embodiments, the computer (125) is a commercially available server, e.g. an IBM System×M5 Tower servers. Computer (125) may be implemented by a processor running software connected to memory and storage. Processor executes instructions, thereby communicating data from a tracking device (160), displaying information related to the tracking, and/or manipulating data. Although described as a single processor, multiple processors may be used according to particular needs. References to processor are meant to include multiple processors where applicable. Memory and storage may include any memory or database module and may take the form of volatile or non-volatile memory including, without limitation, magnetic media, optical media, random access memory (RAM), read-only memory (ROM), removable media, or any other suitable local or remote memory component. The connection of the tracking system computer (125) to the tracking device (160) and/or terminals (120, 175) may be via the internet, internet sub-networks, such as a VPN, or via proprietary network. This connection may also be hardwired to the processor or computer system, for example via cat 5 into a network card, or it can be wireless, for example via GSM, satellite, or WiFi.

Figure 2:
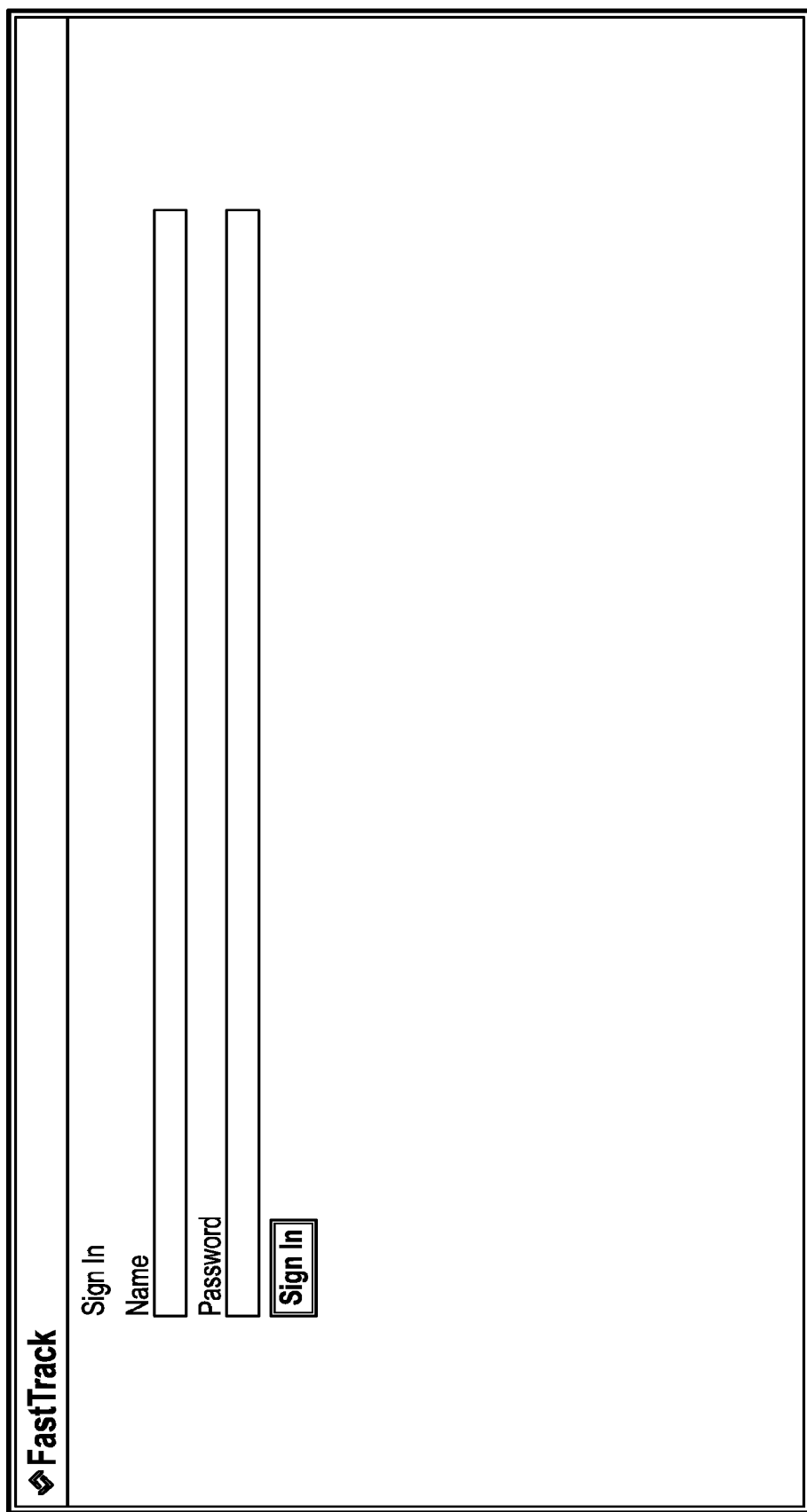
FIG. 2 is a controlled access screen of a tracking system, according to an exemplary embodiment of the present invention.

In exemplary embodiments, the tracking system computer (125) may run software that includes the customizable web application (126). Web application (126) provides a user with administration, reporting, tracking, and search capabilities for all shipments that utilize the device (160). In various implementations, the software may have controlled access, such as a login screen restricting administrator access as seen in FIG. 2. The software may be displayed on a user interface (185). See FIG. 1. User interface (185) may be a monitor connected to the computer (125), or it may be a more remote interacting platform such as an iPad or android tablet device.

Figure 3:
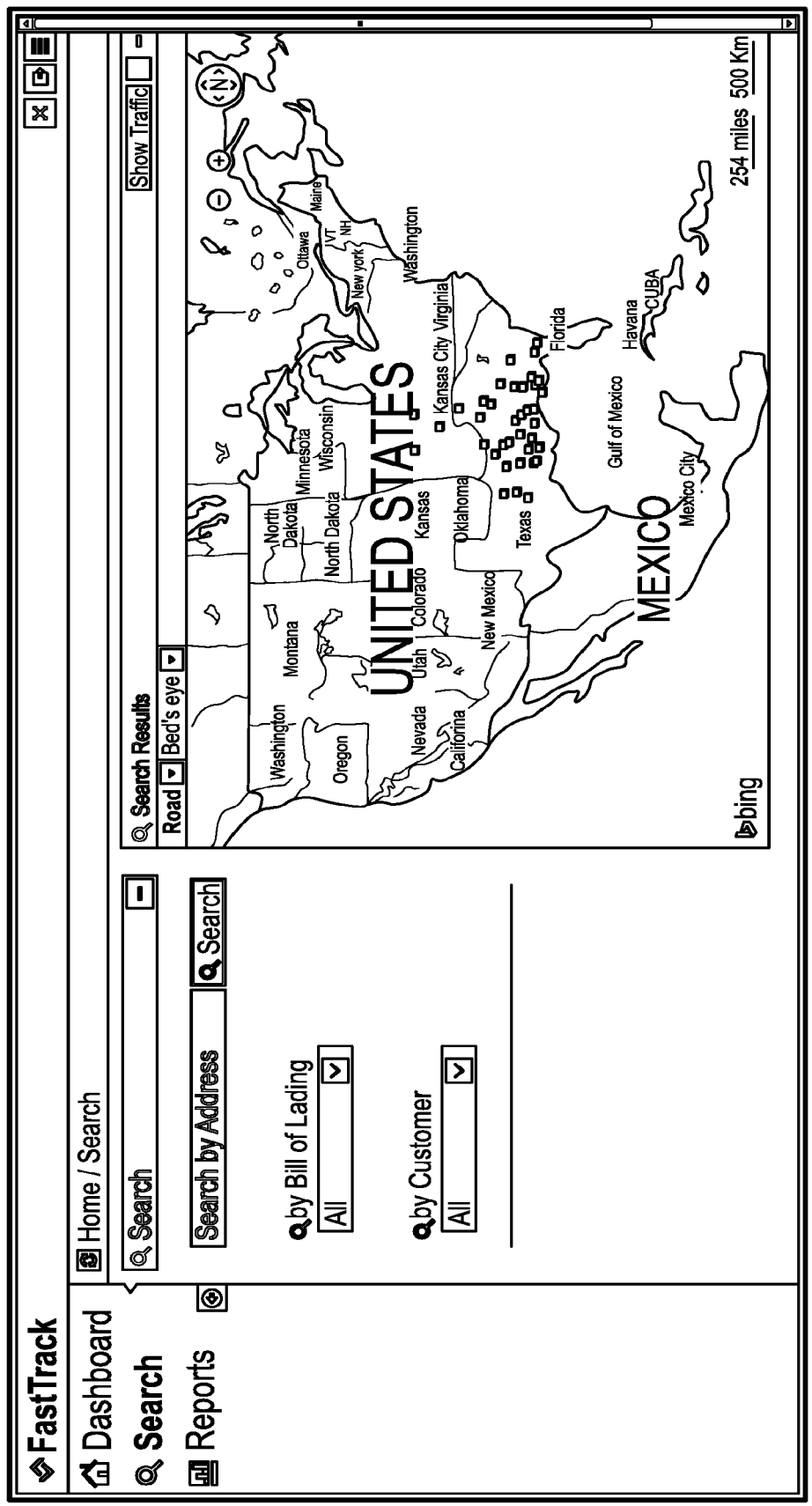
FIG. 3 is a dashboard screen of a tracking system, according to an exemplary embodiment of the present invention.
Figure 4:
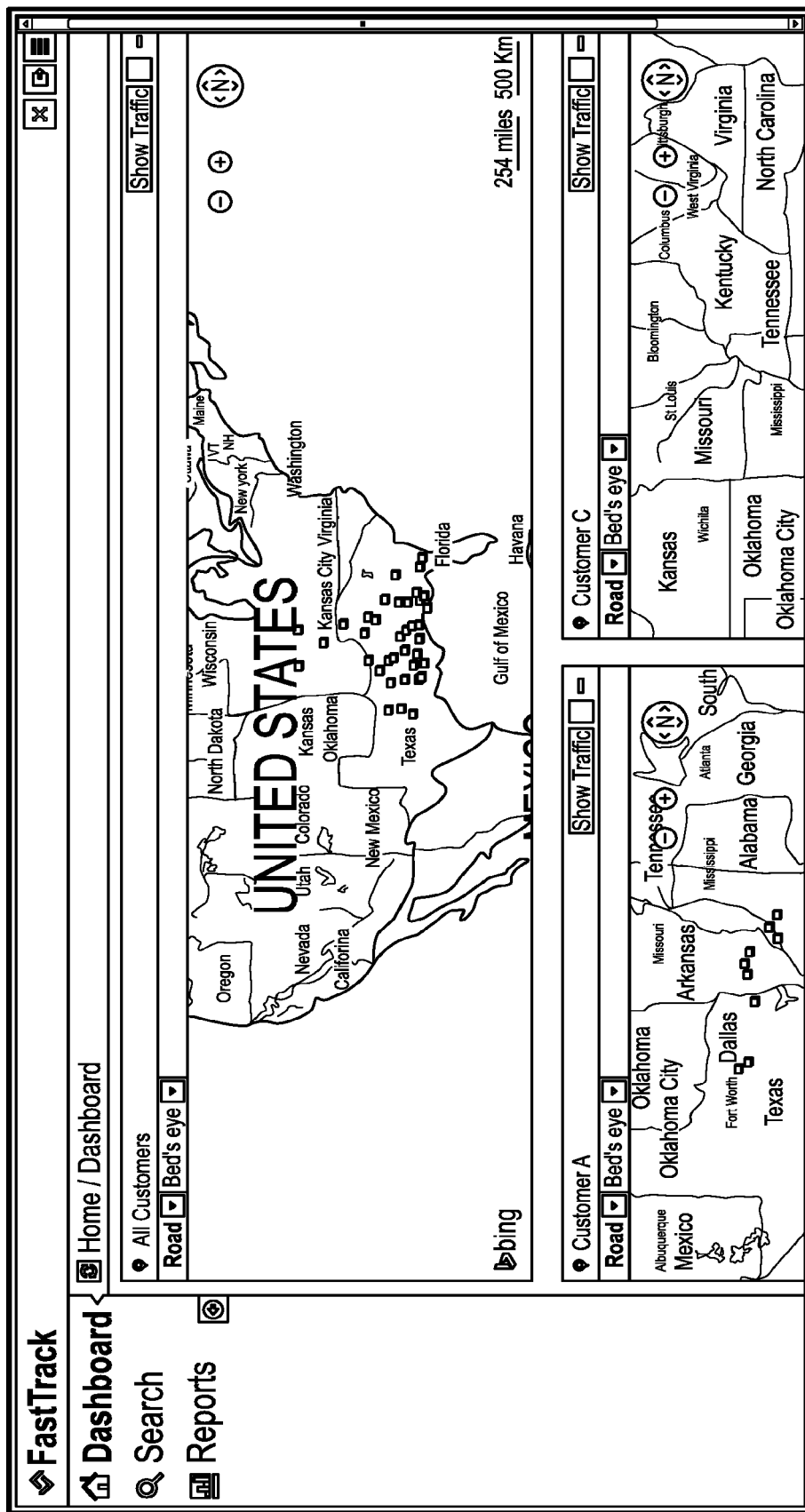
FIG. 4 is a dashboard screen of a tracking system, according to an exemplary embodiment of the present invention.

In various instances, the software may include a dashboard that displays maps, as seen in FIGS. 3 and 4. The map displays may be customizable per individual and/or business needs. A map displayed may be limited to various criterion such as customer or load type, or the map may display the location of all customer shipments. In various instances, the software may allow multiple and/or individual maps to be displayed, and certain maps to be minimized, maximized, and/or rearranged. In the software, the shipments may be represented on the map(s) as clickable truck icons. The truck icons in various instances may be colored green, red, yellow and/or any other colors to indicate shipment status (e.g., green=on schedule, yellow=behind schedule, red=late). Tracking system (10) may establish shipment status based on estimated time of arrival ("ETA") at the destination. On land, the ETA may be derived from current shipment location, the roads (and corresponding speed limits) that must be traversed to reach the destination, and/or the traffic conditions on said roads. At sea, the ETA may be derived from current shipment location, distance to shipment destination, and/or the speed of the shipment. The software may include an interactive function for the truck icons. The clickable truck icons may provide detailed shipment information regarding the status of the shipments. For example, clicking on the icons may open a box listing shipment information including but not limited to bill of lading number, customer name, origin and destination of the shipment, appointment time, ETA, and/or overall status of the shipments indicating whether the shipment is "On Time" or "Delayed." The map in various embodiments may be viewed in road view or satellite view. Also, the administrator may overlay traffic data on map by clicking the "Show Traffic" button.

The tracking system software may further include a smart search function with advanced textual reporting as seen in FIG. 5. This reporting screen may allow users to monitor shipment in real time. Shipment status may be searched for by criterion including, for example, destination address, bill of lading, product, carrier, and/or customer. The search results may display both active and historical loads. The historical data may allow a user to analyze shipment trends by carrier, customer, and/or product. The software may include advanced reporting functions where a user may create customizable reports including defined information such as customer name, shipment/load, and/or status of shipment. Customizable reports may be exported and/or saved as a separate file.

The tracking system software may include an administration screen as seen in FIG. 6 that provides users with the functionality to: create/delete/edit customers, create/delete/edit products, create/delete/edit shipments, assign a tracking device (160) to a shipment, create alerts (for e.g., for arrival, delivery, geofence, motion-detection), and/or create a geofence.

In various embodiments, the tracking system (10) may be integrated into a transportation management system (TMS), located on the same computer or operably connected thereto. The TMS may take parameters from tracking system (10) and use them to manage other elements related thereto. For instance, when generating a cost estimate for a customer, the TMS may screen recent and ongoing trajectories along the route used based on travel time, fuel use, and cost. When planning a route for delivery of freight, the TMS may use the detailed information from the tracking system (10) to see what intersections to avoid, further optimizing overall delivery and pick up. The TMS may also use information related to the evolving position of a load to appropriately schedule a drop off time for the load or schedule a check-in at a remote check-in facility as described in U.S. patent application Ser. No. 14/506,545, filed Oct. 3, 2014, which is incorporated herein by reference in its entirety. Embodiments of the present invention as described herein can be integrated with the various embodiments described in U.S. patent application Ser. No. 14/506,545.

Figure 7:
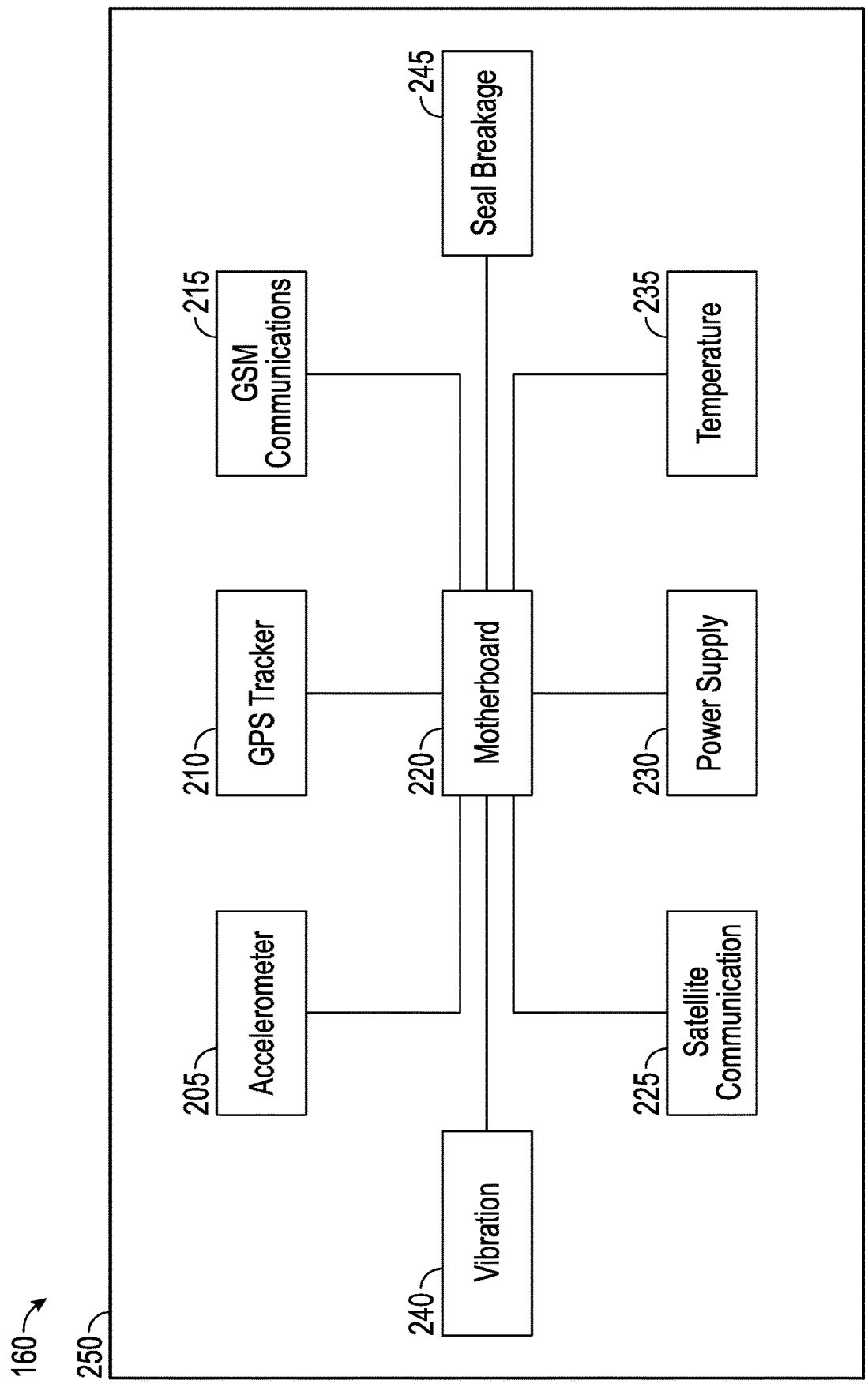
FIG. 7 is a schematic of a tracking device, according to an exemplary embodiment of the present invention.

In various embodiments, the tracking device (160) may take many forms. FIG. 7 shows a schematic of a tracking device (160), according to an exemplary embodiment of the present invention. As depicted, the tracking device (160) includes several components located within a housing (250), including but not limited to an accelerometer (205), GPS tracker (210), GSM communications (215), satellite communications (225), power supply (230) and temperature (235), vibration (240), and seal breakage (245) sensors operably connected to a mainboard (220). In various embodiments, the tracking device (160) may include greater or fewer components and may be configured to weigh less than ten pounds.

Accelerometer (205) may provide local acceleration information to the system (10). Accelerometer (205) may indicate whether the velocity of the tracking device (160) is increasing or decreasing. For example, in a high wind environment, the device (160) may sway causing damage to the components and/or container cargo. Accelerometer (205) may log and monitor these local stresses. Accelerometer (205) may be a variety of accelerometers, including a a LIS344AL (305). See, e.g, FIG. 8. LIS344AL (305) is a low-power three axis linear accelerometer (205) that includes a sensing element and analog IC interface.

For monitoring positioning of the tracking device (160), a GPS tracker (210) may be included in an embodiment of the present invention. GPS tracker (210) may be connected to a variety of systems including but not limited to the Global Positioning System ("GPS'), the Global Navigation Satellite System ("GLONASS"), and/or the BeiDou Navigation Satellite System. GPS tracker (210) has the ability to receive information concerning the latitudinal and longitudinal position of the tracking device (160). GPS tracker may also be configured to translate received latitudinal and longitudinal information into velocity and acceleration. GPS tracker (210) may comprise a variety of trackers, including an Ultimate GPS Module (310) built around the MTK3339 chipset. See, e.g., FIG. 8.

Figure 8:
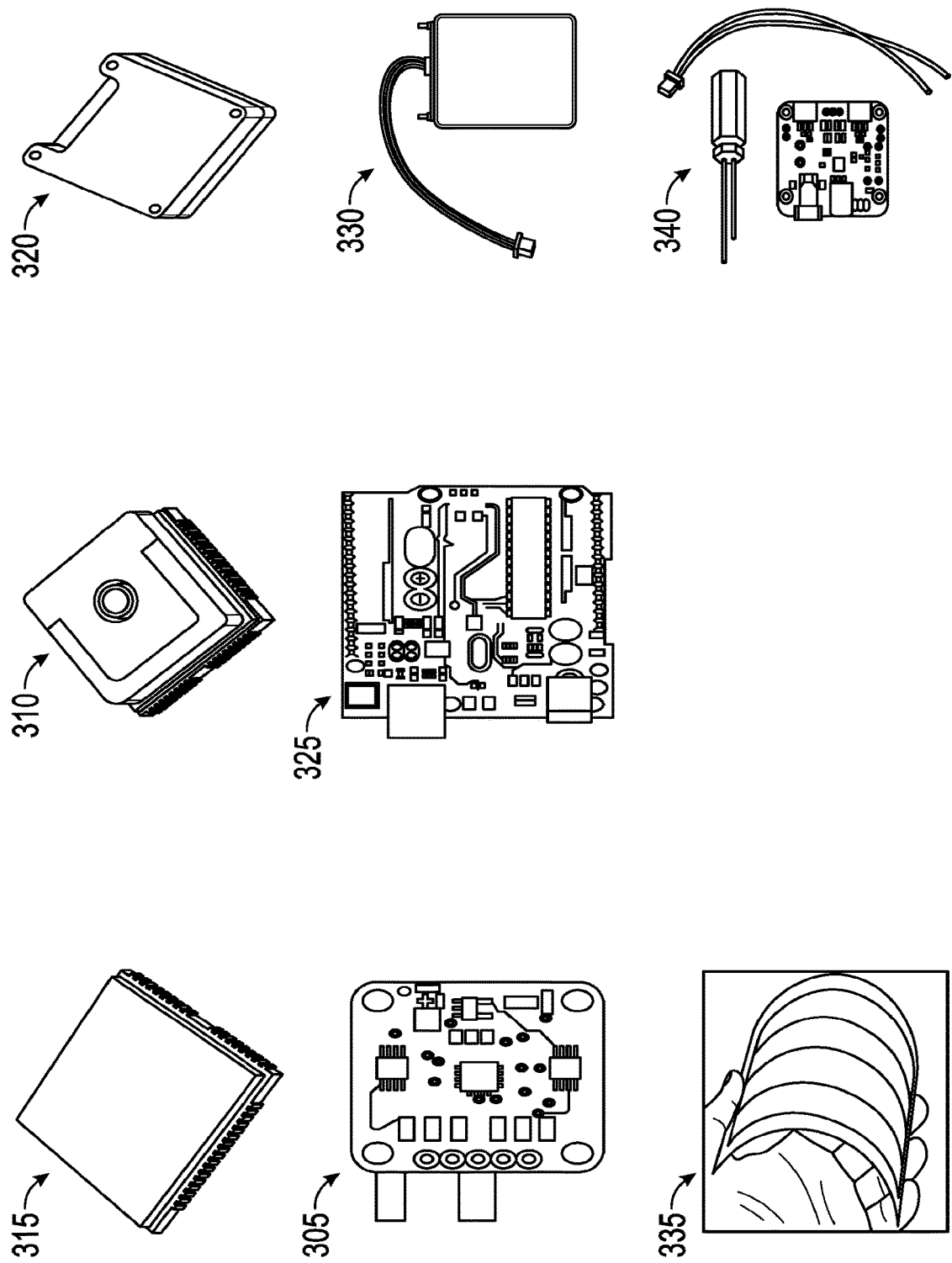
FIG. 8 is a depiction of potential components of the tracking device shown in FIG. 7.

In embodiments of the present invention, the tracking device (160) may be grouped into two versions, a version with satellite communication (225) and a version without satellite communication. A device without satellite communication may communicate with the system (10) via GSM mobile phone networks, but cannot communicate in areas where a GSM mobile phone network is not available. As shown in FIG. 8, GSM communications (215) is a Quectel Quad-band GSM/GPRS MIO Microcontroller (315). On the other hand, a tracking device with satellite communication (225) can use GSM mobile phone networks (primary mode of communication) and/or a satellite network (secondary mode of communication). This allows continuous feedback to the tracking system (10) on transit legs with little to no coverage such as vessel or train. Satellite communications (225) may be a variety of different components such as for instance an Iridium 9602 Satellite Modem (320). See, e.g, FIG. 8. The Iridium 9602 SBD transceiver (320) may provide global tracking via the Iridium satellite network.

Accelerometer (205), GPS tracker (210), GSM communications (215), and/or satellite communications (225) may be operably connected to a mainboard/motherboard (220). Mainboard (220) may allow processing of information from the GPS tracker (210) concerning the location of the tracking device (160) and forwarding said information to the tracking system (10) through the appropriate communications link, e.g. GSM (215) or satellite (220). Mainboard (220) may detect the presence or absence of a GSM signal and thereby control whether the tracking device (160) forwards location information (e.g. from the GPS tracker (210)) to the system via GSM (215) or satellite communication (225). In various instances, the mainboard (220) may encrypt or otherwise protect the tracking information transmitted to prevent interference thereto. Mainboard (220) may be associated with an identifying ID that allows the system to identify the tracking device (160). In various instances, the mainboard (220) may be partially integrated with each of the various components of the tracking device (160) or may comprise a separate component. In various embodiments, the mainboard (220) may take many forms, for example, an Arduino UNO Rev3 (325) as shown in FIG. 8.

Power for the mainboard (220), accelerometer (205), GPS tracker (210), GSM communications (215), satellite communications (225) and/or other components of the tracking device (160) may flow directly from the power supply (230) to the individual components or via the mainboard (220). In various instances, the power supply (230) may be configured to send to the tracking system (10) via the mainboard (220) and communications indications of remaining power. In various instances, power may be continuous or it may be regulated by a switch or other mechanism. Power supply (230) may take on a variety of different forms, such as a battery, depending on the design of the tracking device (160). In an embodiment, the power supply (230) is a Lithium Ion Polymer Battery—3.7 v 1200 mAh (330), as shown in FIG. 8. In an additional embodiment, the power supply (230) includes a battery as well as a solar panel to recharge the battery during daylight hours. As seen in FIG. 8, the solar panel may be a Flexible 6V 1 W Solar Panel (335) with the connection to the battery facilitated by, for example, USB/DC/Solar Lithium Ion/Polymer charger—v2 (340).

Depending on application needs, the tracking device (160) may further include additional sensors such as temperature (235), vibration (240) and seal breakage (245) sensors, all optionally connected to the mainboard/motherboard (220), communications, and/or power supply (230). Temperature sensor (235) may be configured to measure the temperature outside the device (160) or inside the device (160). Vibration sensor (240) may measure vibration information that may then be used by the device (160) and/or tracking system (10) to determine cargo movement and integrity. Seal breakage sensor (245) may be connected to a bolt seal, wire/tie seal, and/or other type of seal. In various instances, the seal sensor (245) may be a conductance based sensor such as a reed switch. The reed switch may be attached to both ends of bolt locking mechanism. When the bolt locking mechanism is locked, the circuit of the reed switch is closed, and when unlocked the circuit may be opened.

Tracking device (160) may be configured to lock within existing plastic, metal, cable, or padlock seals. Alternatively, tracking device (250) may be designed to lock within existing bolt and/or wire/tie seals.

Tracking system (10) may include plastic, metal, cable, and/or padlock seals. These seals may be configured to pass through an aperture of the tracking device (160) as well as a central hole of overlapping flanges of a container door. These seals may include numbering unique to a load and/or customer and be configured to blush if tampered with. In some instances, these seals may include a ball locking mechanism that is difficult/impossible to reseal once broken. Examples of such seals include S-13677, H-541, and H-1346 from Uline™.

Figure 9:
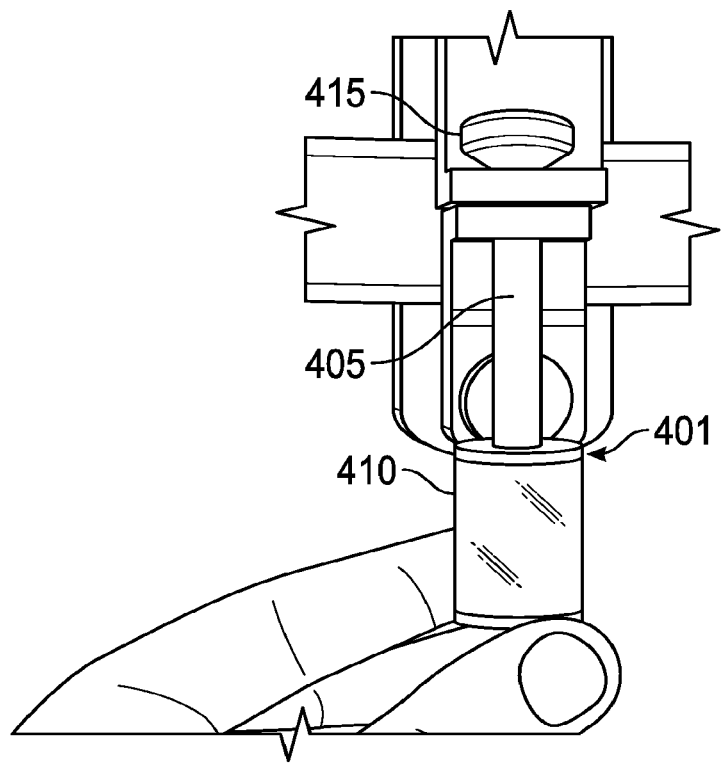
FIG. 9 is a front view of a bolt seal, according to an exemplary embodiment of the present invention.
Figure 10:
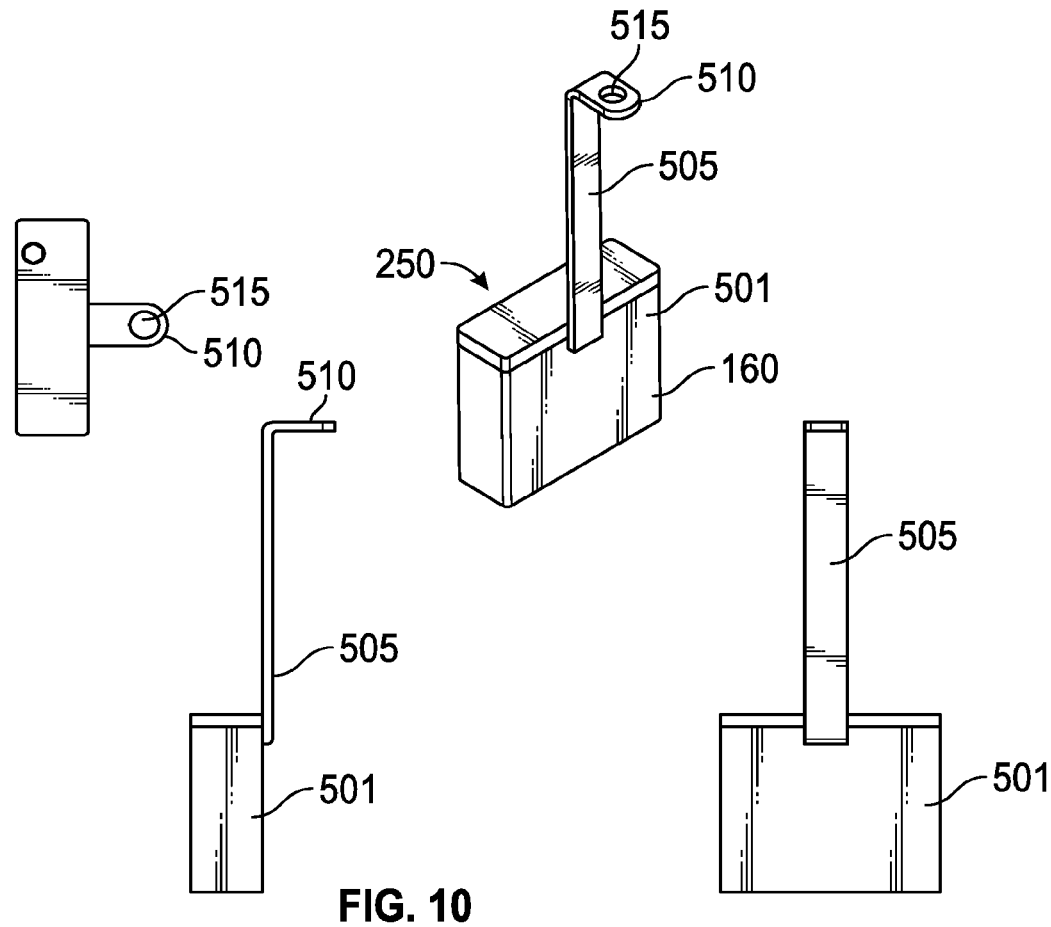
FIG. 10 is a depiction of top, front, right, and isometric views of a housing of a tracking device, according to an exemplary embodiment of the present invention.
Figure 11:
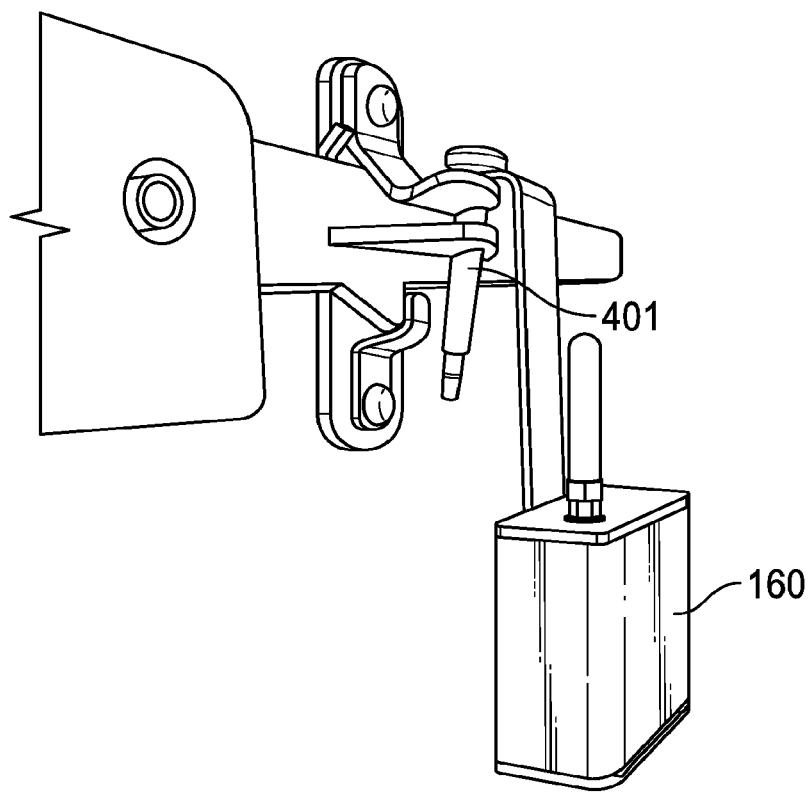
FIG. 11 is a side isometric view of a tracking device without a secured seal, according to an exemplary embodiment of the present invention.
Figure 12:
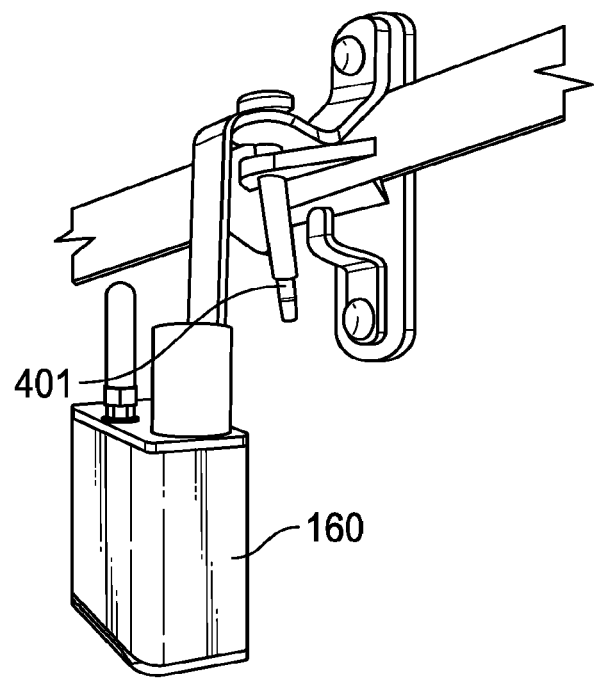
FIG. 12 is a side isometric view of the tracking device shown in FIG. 11.
Figure 13:
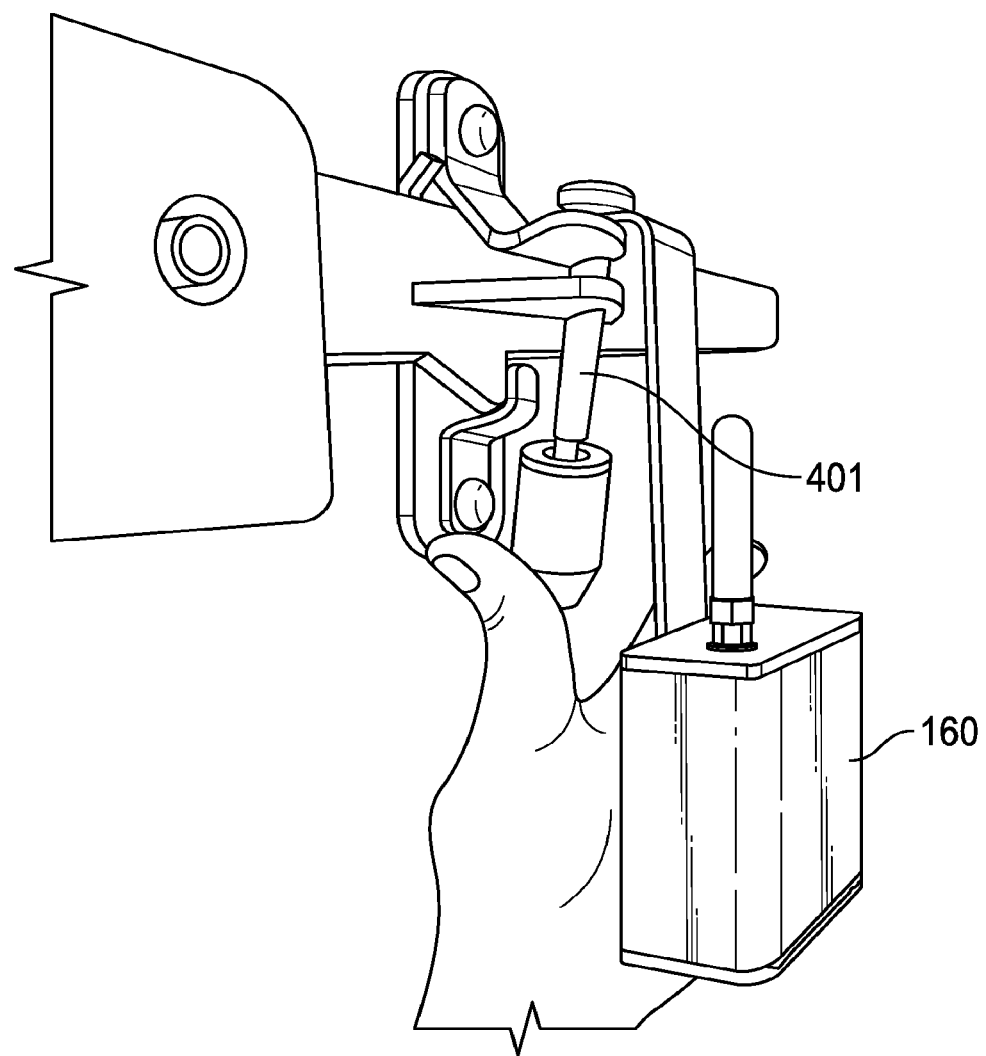
FIG. 13 is a side isometric view of the tracking device shown in FIG. 11 with the seal being secured, according to an exemplary embodiment of the present invention.

In other embodiments, the tracking system (10) may include a bolt seal (401). Bolt seals (401) come in a variety of forms. A commercially available bolt seal (401) is shown in FIG. 9. Depending upon the shipping company/application, a different bolt seal (401) may be used. Bolt seals (401) may comprise a bolt (405) with a head (415) and a locking mechanism (410). Bolt seal (401) may lock a container (135) and bill of lading (190) of system (10) disclosed herein, therein preventing access thereto without breaking the bolt seal (401).

As seen in FIGS. 10, 11, 12, and 13, tracking device (160) includes a housing (250). Housing (250) may be specially tailored to a unique transit application. In some instances, the housing (250) may include a connector (510), a support member (505), and a main body (501). In various embodiments, the tracking device housing (250) may be formed from plastic (e.g. PVC), metal, or other suitable materials.

Connector (510) may be adjustable for receiving different types of seals. Connector (510) may be designed to attach to the seal (401) via an aperture (515) so that the tracking device (160) cannot be removed from the seal (401) without breaking the seal (401). Aperture (515) may be large enough for this purpose yet small enough to derive stability for the positioning of the tracking device (160) from the seal (401) (e.g. to limit swaying and other movement of the tracking device (160) that may damage device integrity). In various embodiments, the connector (510) and connector aperture (515) may be dimensioned to fit on a bolt seal bolt (405) between the head (415) and the locking mechanism (410). In various examples, a seal sensor (245) may be tied to the aperture (515) and extend to the connector (510) exterior. In exemplary embodiments, connector (510) has a width of 1 inch and a thickness of 0.13 inches, while the aperture (515) of the connector (510) has a width of 0.38 inches.

Connector (510) may be conjoined with a support member (505). Support member (505) may link the connector (510) to the housing main body (501). The length and geometry of the support member (505) may vary. For example, support member (505) may appear arm-like and extend from the main body (501). See, e.g., FIG. 10. In various embodiments, the tightness of the seal connector (510) connection and the support member's (505) rigidity may act to limit device (160) movement in transit. For example, as seen in FIGS. 10, 11, 12, and 13, the support member (505) may be linked to a connector (510) sandwiched within the bolt seal (401) with the integrity of the bolt seal (401) connection and rigidity of the support member (505) acting to substantially limit swaying and thereby protecting integrity of the tracking device (160). In exemplary embodiments, support member (505) has a 5 thickness of 0.13 inches and a total height of 4.5 inches, including 0.5 inches of overlap with the main body (501).

Main body (501) may house the mainboard (220) and other important circuitry of the tracking device (160). Main body (501) may take a variety of forms depending on the included circuitry and intended application. In exemplary embodiments, the height of the housing (250) is 6.5 inches, the main body (501) being 2.5 inches and the connector (505) being 4 inches. Main body (501) may have a width of 1 inch and a length of 3 inches.

As shown in FIG. 1, tracking device (160) may be placed on a container (135) and continuously interact with the tracking system (10). Tracking system (10) receives information from the tracking device (160) such as latitude, longitude, acceleration, and/or battery life and makes this information usable to an administrator. Tracking system (10) may include a computer (125) running software operatively connected to the tracking device (160), a user interface (185), and optionally, local warehouse terminals (120, 175).

Figure 14A:
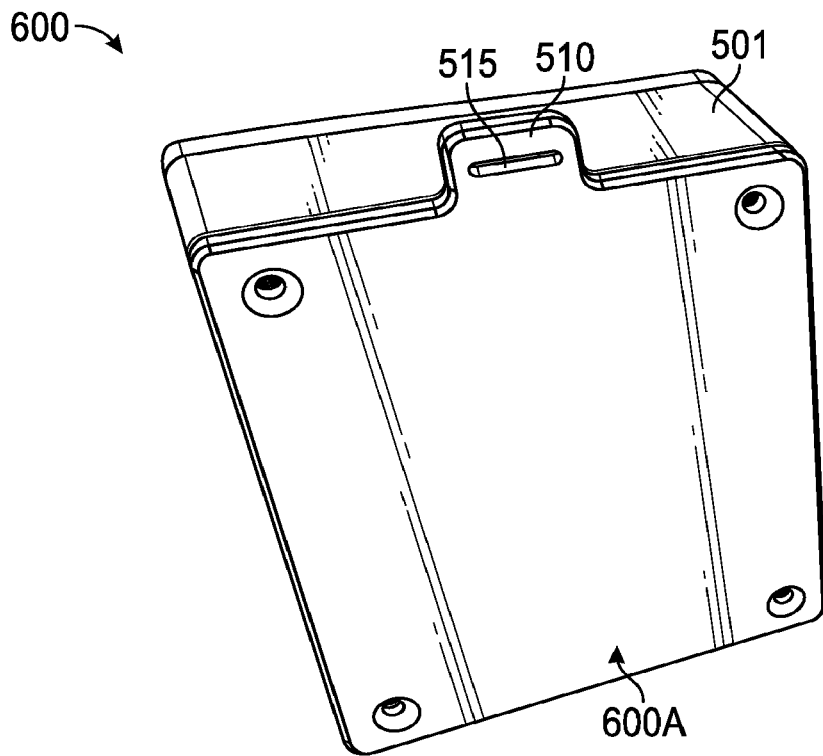
FIG. 14A is a rear isometric view of a tie mount housing of a tracking device, according to an exemplary embodiment of the present invention.
Figure 14B:
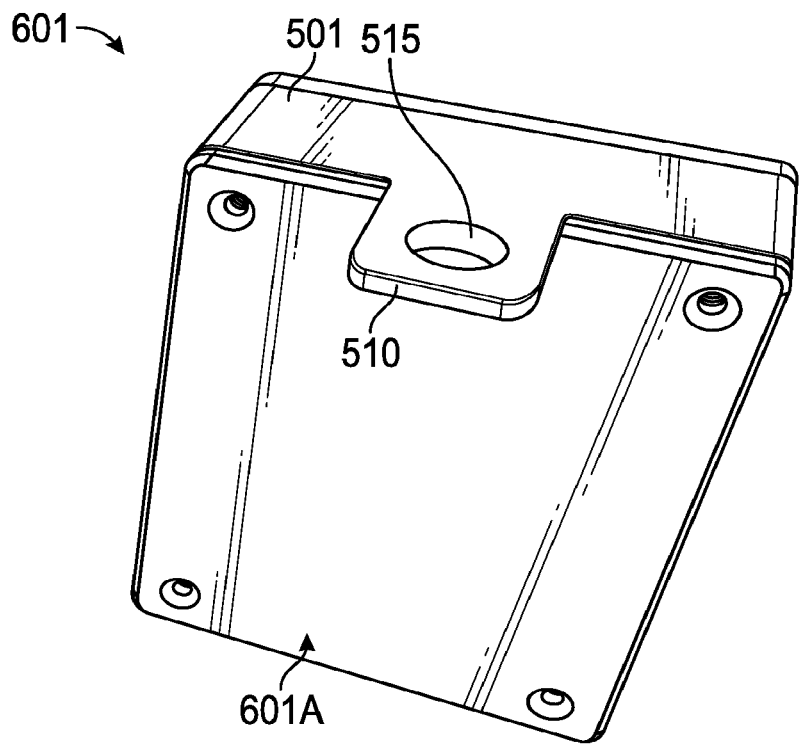
FIG. 14B is a rear isometric view of a bolt mount housing of a tracking device, according to an exemplary embodiment of the present invention.
Figure 15A:
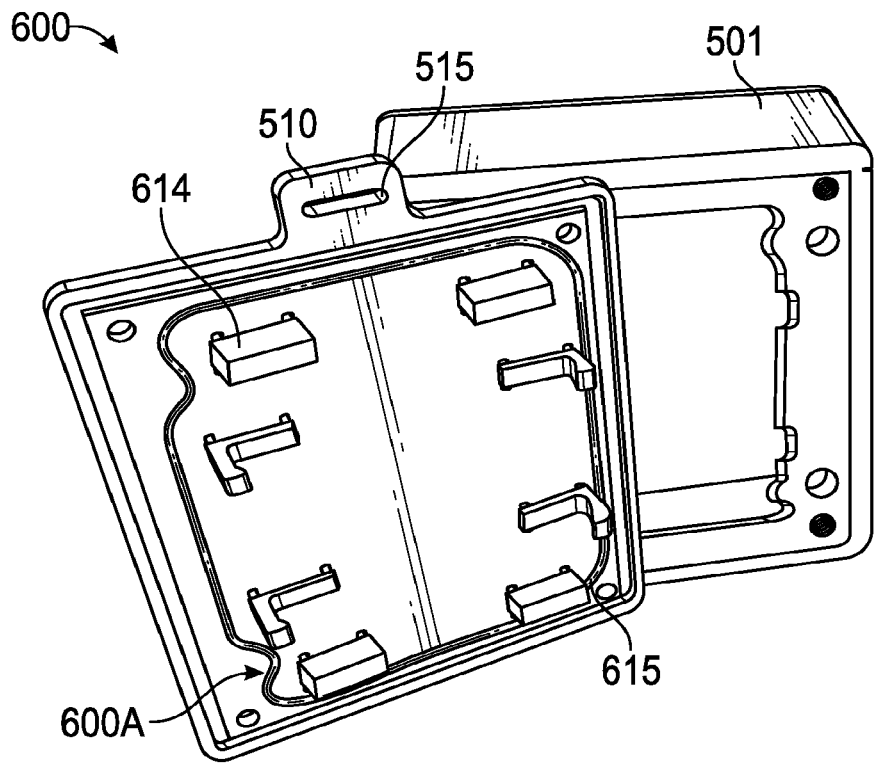
FIG. 15A is a rear isometric view of the tie mount housing shown in FIG. 14A with an access cover removed, according to an exemplary embodiment of the present invention.
Figure 15B:
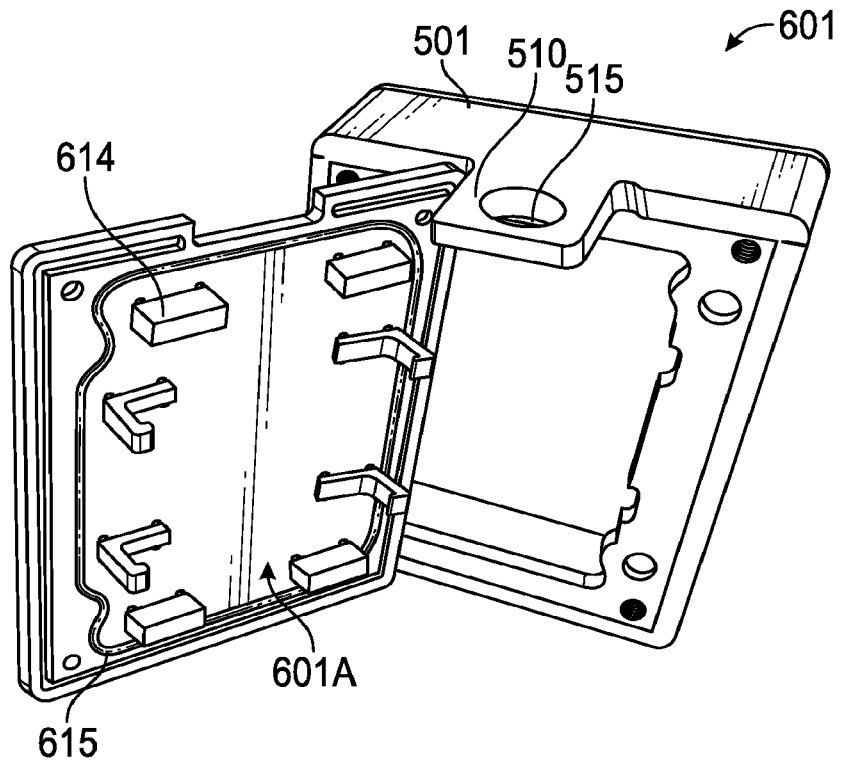
FIG. 15B is a rear isometric view of the bolt mount housing shown in FIG. 14B with an access cover removed, according to an exemplary embodiment of the present invention.
Figure 16:
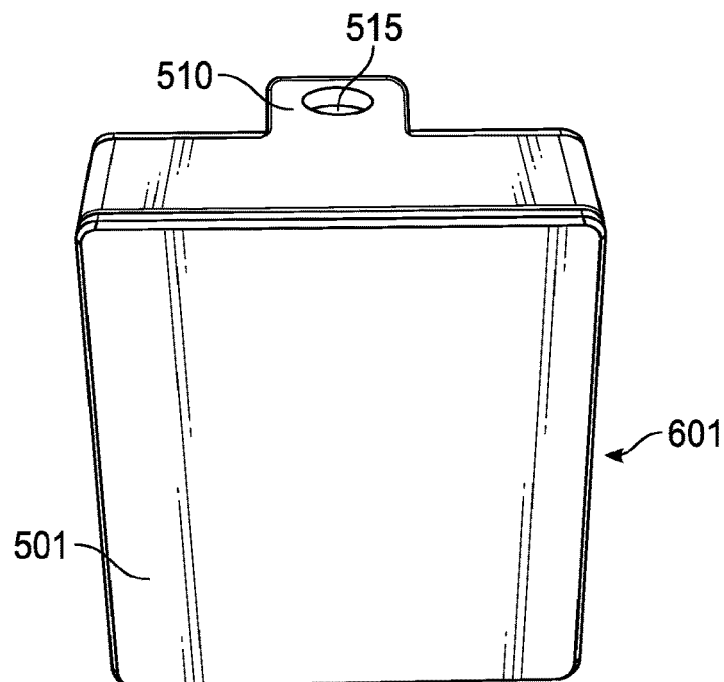
FIG. 16 is a front isometric view of the bolt mount housing shown in FIG. 14B.
Figure 17:
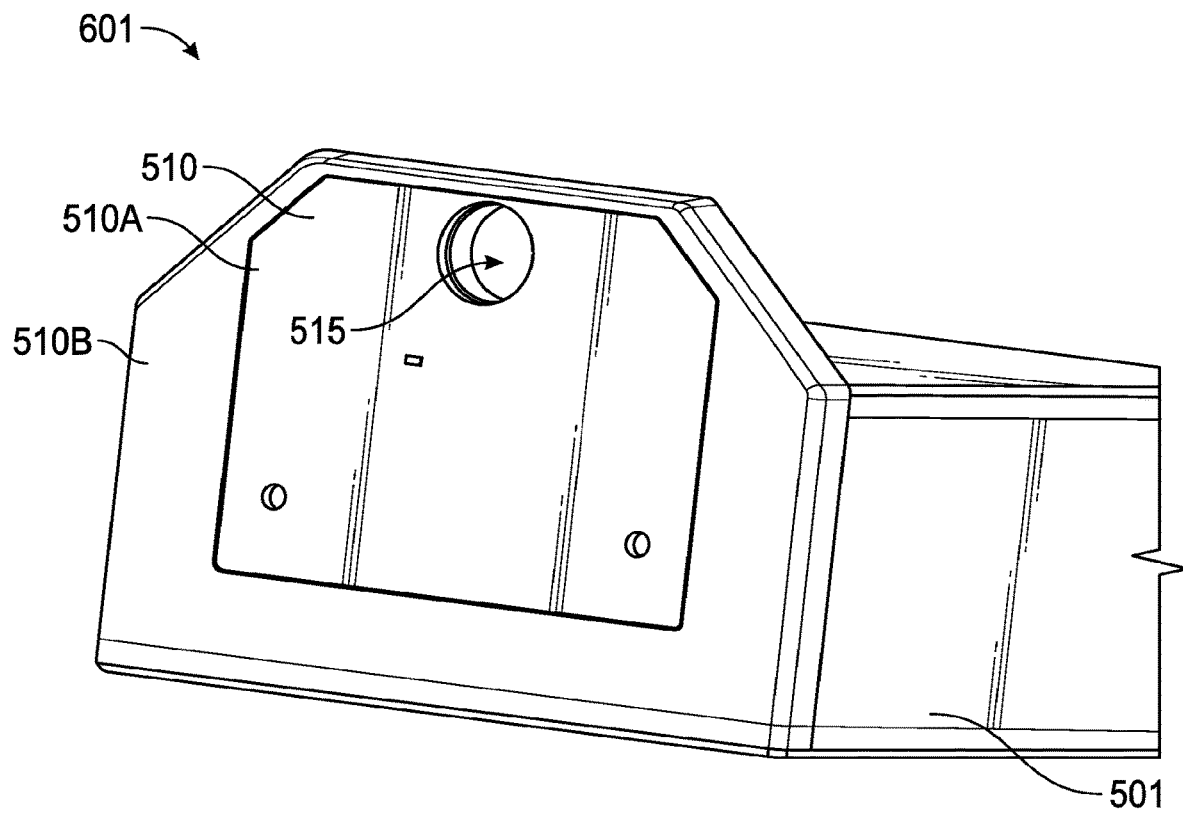
FIG. 17 is an enlarged broken isometric view of a bolt mount housing, according to an exemplary embodiment of the present invention.

Referring to FIGS. 14A and 14B, alternative embodiments of a tie mount housing (600) and a bolt mount housing (601) of a tracking device are shown. FIGS. 15A and 15B show the tie mount and bolt mount housings (600, 601) with respective access covers (600A, 601A) removed. FIG. 16 is a front isometric view of the bolt mount housing (601) shown in FIG. 14B. FIG. 17 is an enlarged broken isometric view of another embodiment of a bolt mount housing (601).

Tie mount and bolt mount housings (600, 601) represent improved embodiments of housing (250) of tracking device (160). Embodiments of the present invention are not limited to the particular configurations of housings (600, 601) described herein, and may have any other shape and/or configuration. Tie mount housing (600) is designed to lock within wire/tie seals. Bolt mount housing (601) is designed to lock within bolt seals, for example bolt seal (401) described herein. Tie mount and bolt mount housings (600, 601) each have substantially the same features as housing (250), including but not limited to main body (501), connector (510), and connector aperture (515). Unlike housing (250), however, tie mount and bolt mount housings (600, 601) do not include a support member (505) linking connector (510) to main body (501). Rather, connector (510) is attached and integrated directly to main body (501).

Tie mount and bolt mount housings (600, 601) each include removable access covers (600A, 600B) for covering/protecting internal components of tracking device (160), and to allow for easy access to the components. As shown in FIG. 15A, connector (510) of tie mount housing (600) is directly attached to and integrated with access cover (600A), in a plane parallel to main body (501). In other embodiments, connector (510) of tie mount housing (600) may be directly attached to main body (501). As shown in FIG. 15B, connector (510) of bolt mount housing (601) is directly attached to and integrated with main body (501), in a plane perpendicular to main body (501). In other embodiments, connector (510) of bolt mount housing (601) may be directly attached to access cover (601A).

Connector aperture (515) of tie mount housing (600) has a substantially rectangular/slit shape for locking within wire/tie seals. See, e.g., FIG. 14A. Connector aperture (515) of bolt mount housing (601) has a circular shape for locking within bolt seals. See, e.g., FIG. 14B. In other embodiments, connector apertures (515) of tie and bolt mount housings (600, 601) may have any other shape suitable for locking within wire/tie and/or bolt seals. Barring the conflicting planar orientation of the connector (510), as well as the shape of the aperture (515), tie mount housing (600) and bolt mount housing (601) have identical features as disclosed herein.

As shown, tie mount and bolt mount housings (600, 601) are made of plastic. In other embodiments, tie mount and bolt mount housings (600, 601) may be hybrid metal and plastic units. See, e.g., FIG. 17. In this embodiment, connector (510) includes a plastic piece 510B and a metal piece 510A having a circular aperture (515). Metal piece 510A is integrated with plastic piece 510B and main body 501 to reinforce and strengthen housing (601) such it may not be tampered with and may withstand rough movement while being transported. In other embodiments, tie mount housing (600) may include a metal piece having a substantially rectangular aperture. Although shown in this particular configuration, housings (600, 601) may be made of any other materials to provide strength and stability. As shown in FIG. 17, connector (510) has a trapezoid shape. Alternatively, connector (510) may have any other shape to provide stability in attaching to bolt and/or wire/tie seals.

Figure 18:
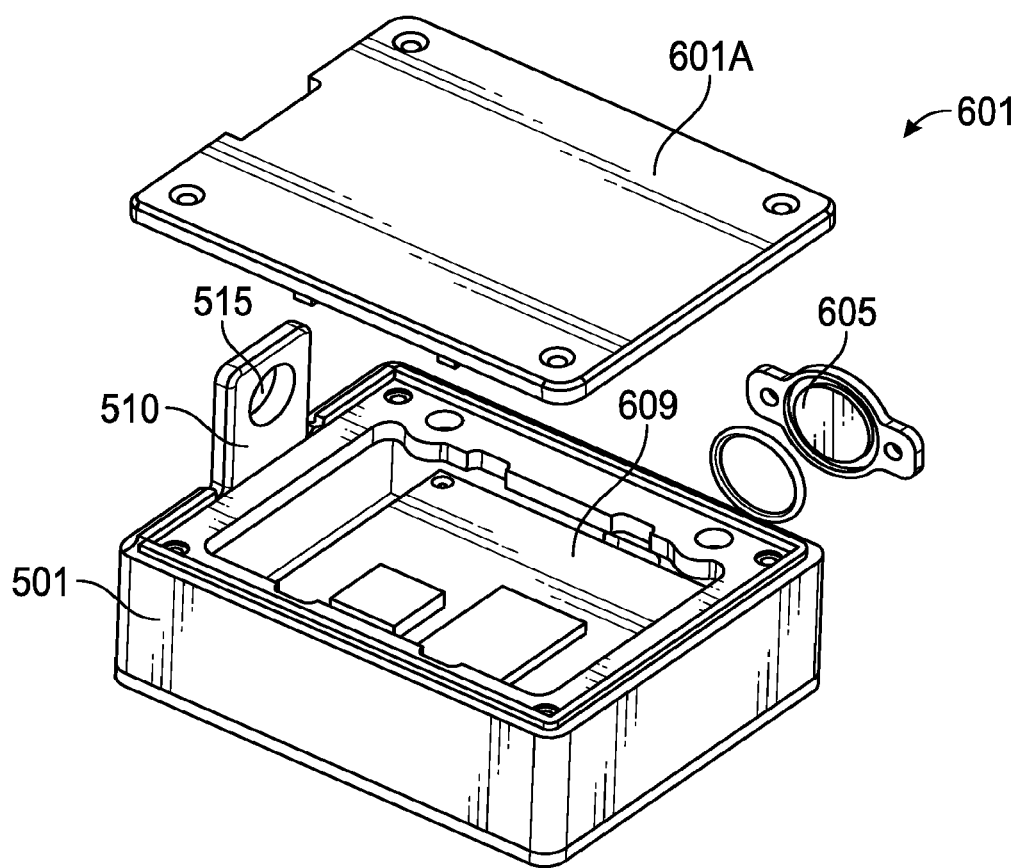
FIG. 18 is an exploded isometric view of the bolt mount housing shown in FIG. 14B with an access cover and charging port cover removed, according to an exemplary embodiment of the present invention.
Figure 19:
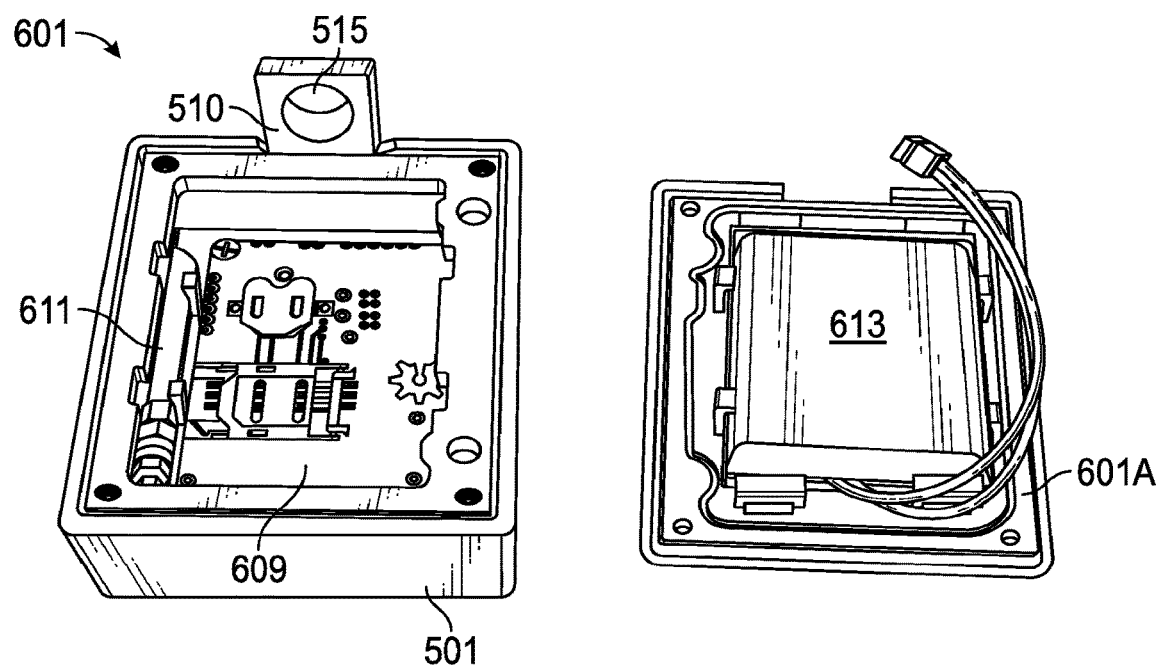
FIG. 19 is a top isometric view of the bolt mount housing shown in FIG. 18 with a circuit board and antenna mounted within the housing and battery mounted to the access cover, according to an exemplary embodiment of the present invention.
Figure 20:
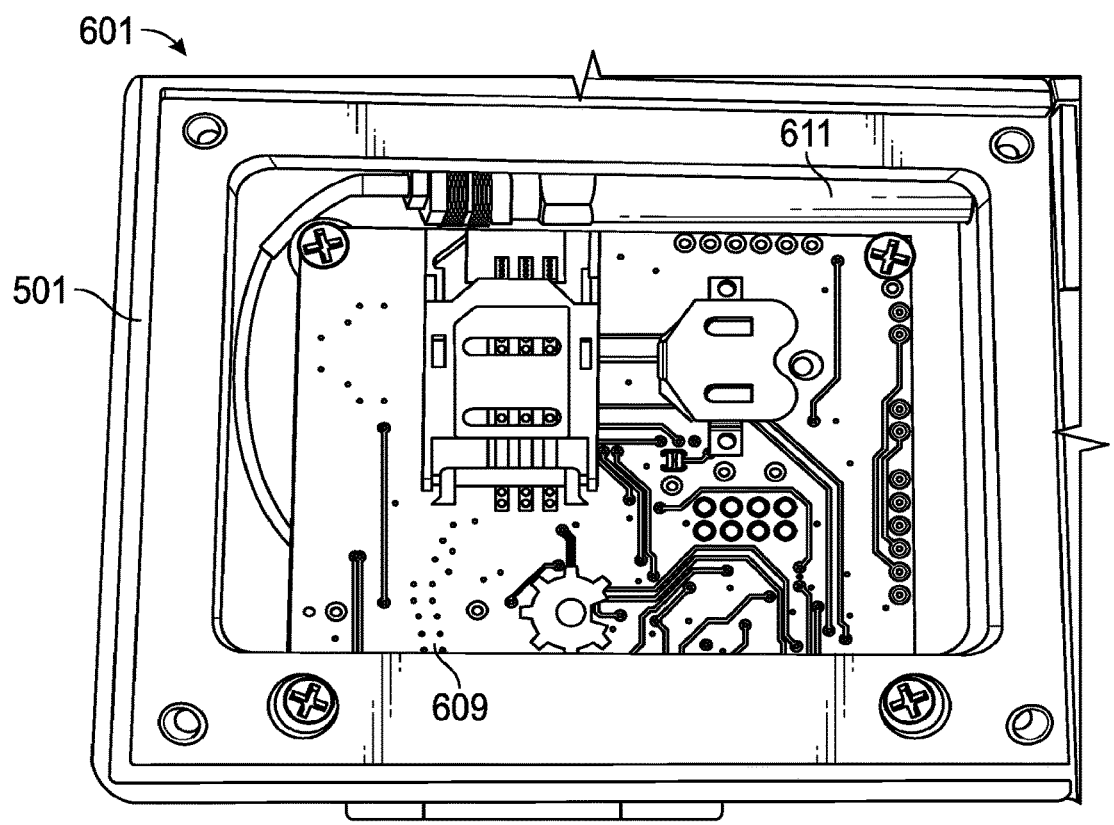
FIG. 20 is a top view of the circuit board and antenna mounted within the housing shown in FIG. 19.
Figure 21:
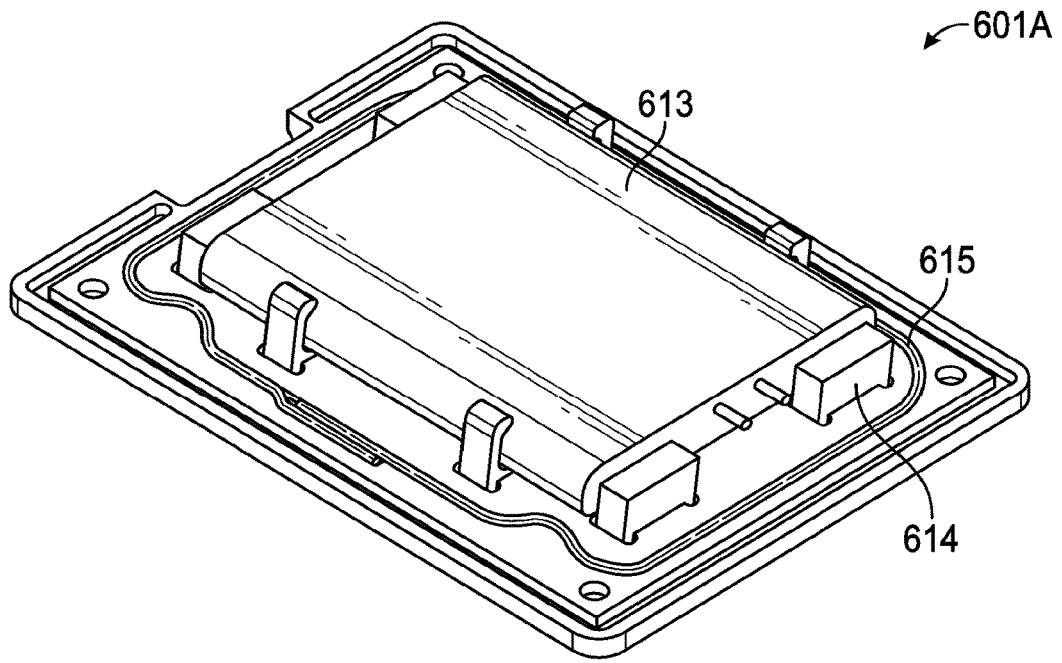
FIG. 21 is an isometric view of the battery mounted to the access cover shown in FIG. 19.

FIG. 18 is an exploded isometric view of the bolt mount housing (601) with the access cover (601A) and a charging port cover (605) removed. FIG. 19 is a top isometric view of the bolt mount housing (601) with a circuit board (609) and antenna (611) mounted within the housing (601), and battery (613) mounted to the access cover (601A). FIG. 20 is a top view of the circuit board (609) and antenna (611) mounted within the housing (601). FIG. 21 is an isometric view of the battery (613) mounted to the access cover (601A).

As shown in FIGS. 19 and 20, bolt mount housing (601) includes printed circuit board (PCB) (609) and antenna (611) mounted within main body (501). Although not shown, bolt mount housing (601) may include additional components of tracking device (160) disclosed herein, including but not limited to an accelerometer (205), GPS tracker (210), and temperature (235), vibration (240), and seal breakage (245) sensors operably connected to the PCB (609).

Battery (613) is attached to interior of access cover (601A) to charge device (160) while being transported. See FIGS. 19 and 21. Access cover (601A) includes battery stops (614) to hold battery (613) in place. See FIG. 21. In other embodiments, battery (613) may be mounted within main body (501). Battery (613) may be a lithium-ion (Li-ion) battery. Alternatively, battery (613) may be a battery with over 2.5 times the battery life of Li-ion batteries. In some embodiments, battery (613) may be charged via magnetic induction. In this embodiment, a coil of wire and magnets may be placed around and/or within housing (250, 600, 601) of tracking device (160) such that movement of tracking device (160) while bring transported will recharge the device (160). Magnets may be placed within housing (250, 600, 601) such that they may move around. Per Faraday's Law, any change in the magnetic environment (magnetic field and magnetic flux) of the coil of wire will cause a voltage (emf) to be induced in the coil. No matter how the change is produced, the voltage will be generated. The change may be produced in several ways, including but not limited to changing the magnetic field strength, moving a magnet toward or away from the coil, moving the coil into or out of the magnetic field, and rotating the coil relative to the magnet. So, for example, voltage may be generated/induced when the tracking device (160) and coil, both integrated with and securely attached to a seal and/or container, as well as the magnets contained within the housing (250, 600, 601) of device (160), sway while bring transported by the container.

In other embodiments, tracking device (160) may be charged via supercapacitors (also known as ultracapacitors or double-layer capacitors) configured to serve as a battery replacement for improved overall battery life. Basic capacitors such as electrostatic and electrolytic capacitors generally store energy by means of a static charge as opposed to an electrochemical reaction. Applying a voltage differential on the positive and negative plates charges the capacitor. Supercapacitors have a much higher capacitance than basic capacitors. Supercapacitors are ideal for energy storage that undergoes frequent charge and discharge cycles at high current and short duration. Although generally confined to between 2.5 and 2.7V, several supercapacitors may be connected in series to achieve higher voltages. Charge time of a supercapacitor is about 10 seconds, compared to about 10 to 60 minutes for Li-ion batteries. Supercapacitors can also be charged and discharged virtually an unlimited number of times.

Gasket (615) runs along the perimeter of the access cover (601A). See FIG. 21. Gasket (615) is utilized to make the housing (601) water-tight. Gasket (615) is made of rubber. Alternatively, housing (601) may have any other configuration to perform the same function.

Figure 22:
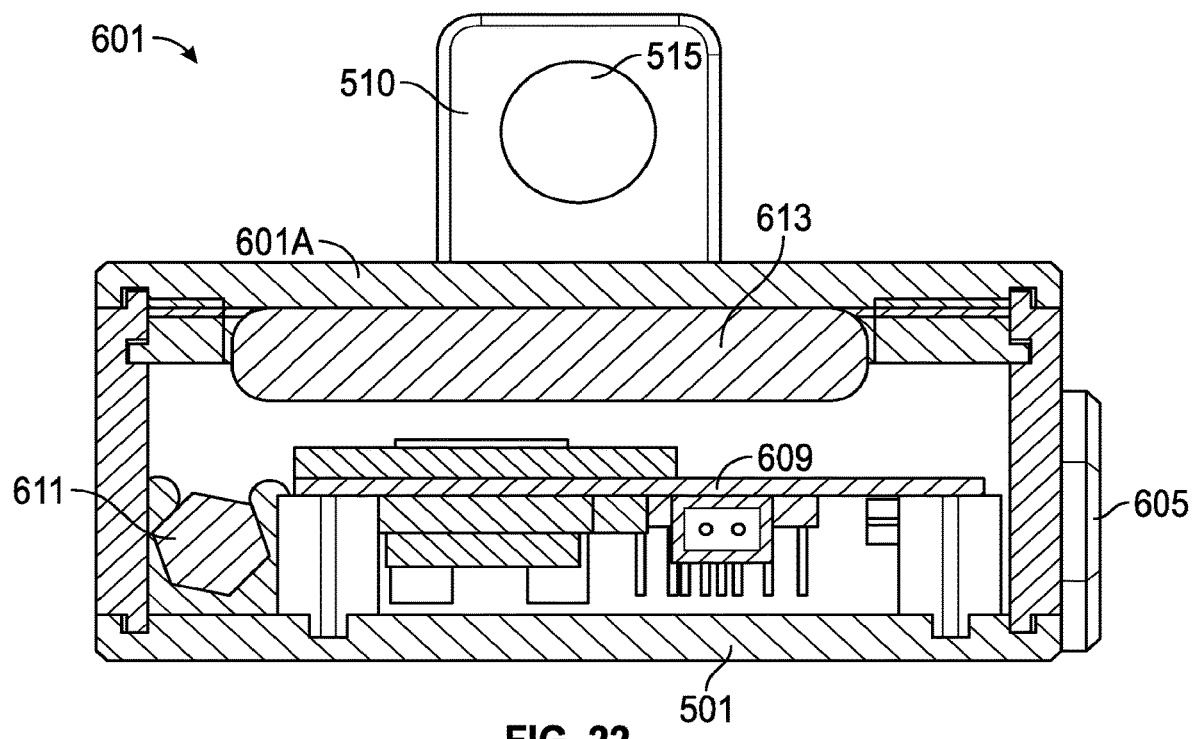
FIG. 22 is a cutaway view of the top of the bolt mount housing shown in FIG. 14B.
Figure 23:
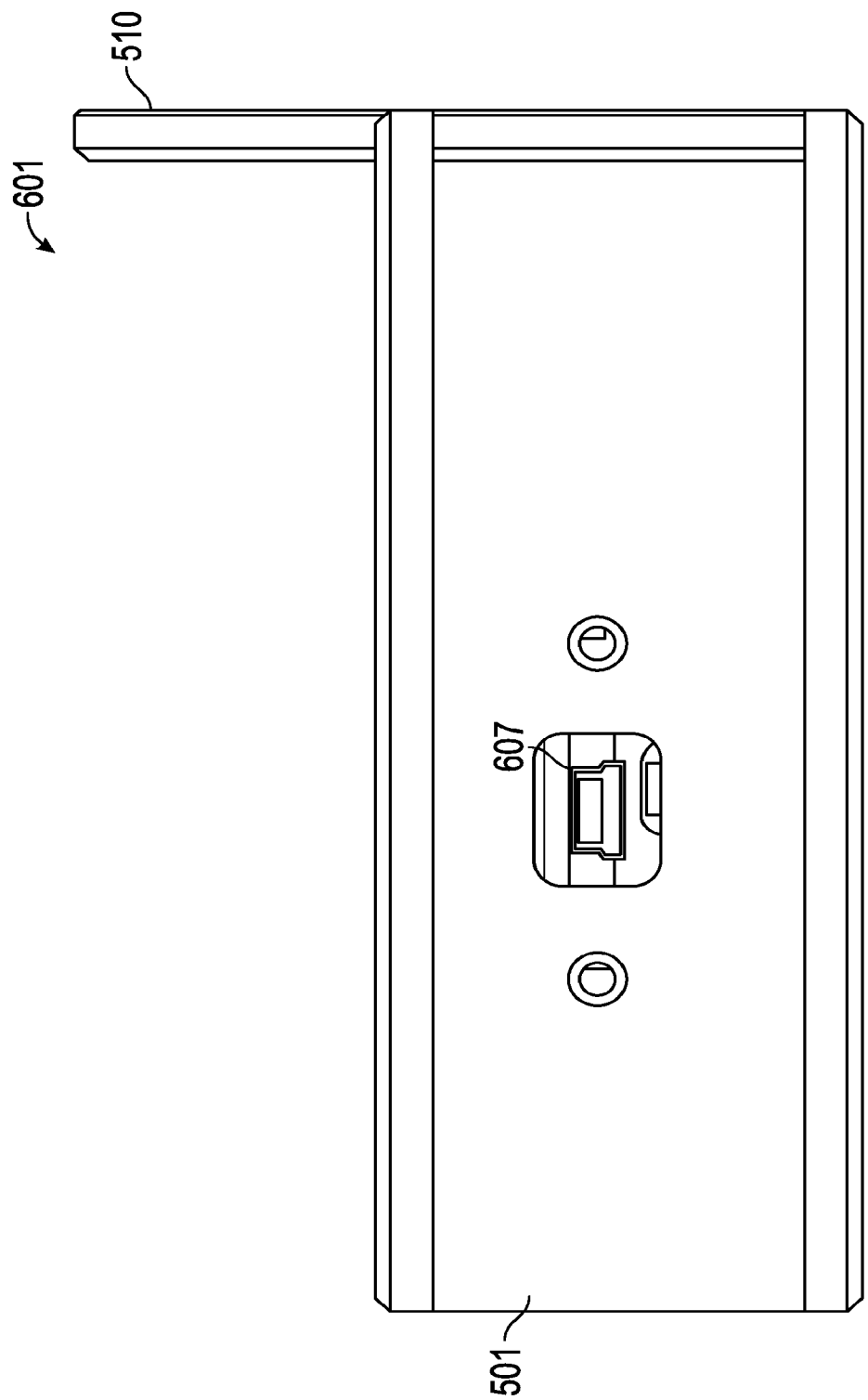
FIG. 23 is a close-up view of a charging port of the bolt mount housing shown in FIG. 18 with the charging port cover removed, according to an exemplary embodiment of the present invention.

FIG. 22 is a cutaway view of the top of the bolt mount housing (601). FIG. 23 is a close-up view of a charging port (607) of the bolt mount housing (601) with the charging port cover (605) removed. As shown in FIG. 23, charging port (607) is a (micro) USB port located on the side of the main body (501). In other embodiments, charging port (607) may be any other port configured to charge/re-charge tracking device (160) and/or components in housing (600) when device (160) returns to the facility and/or is not being transported. Charging port cover (605) is provided to cover charging port (607). See FIGS. 18 and 22. Charging port cover (605) is removable. In this embodiment, charging port cover (605) also includes a plastic ring (O-ring), both of which are screwed onto main body (501) via inserts adjacent to charging port (607). See FIG. 23. In other embodiments, charging port (607) may not be included on main body (501). Rather, a separate wireless charging device may be provided to charge device (160) when device (160) returns to the facility and/or is not being transported. The wireless charging device may use "Qi" inductive charging technology to charge device (160). The Qi system generally includes a power transmission pad and a compatible receiver in a portable device. To use the Qi system, the portable device is placed on top of the power transmission pad, which charges it via resonant inductive coupling. Examples of wireless charging devices that may be used include commercially available devices such as LG WCP-300 wireless charger, Energizer® Dual Inductive Charger, and Duracell Powermat®.

Figure 24:
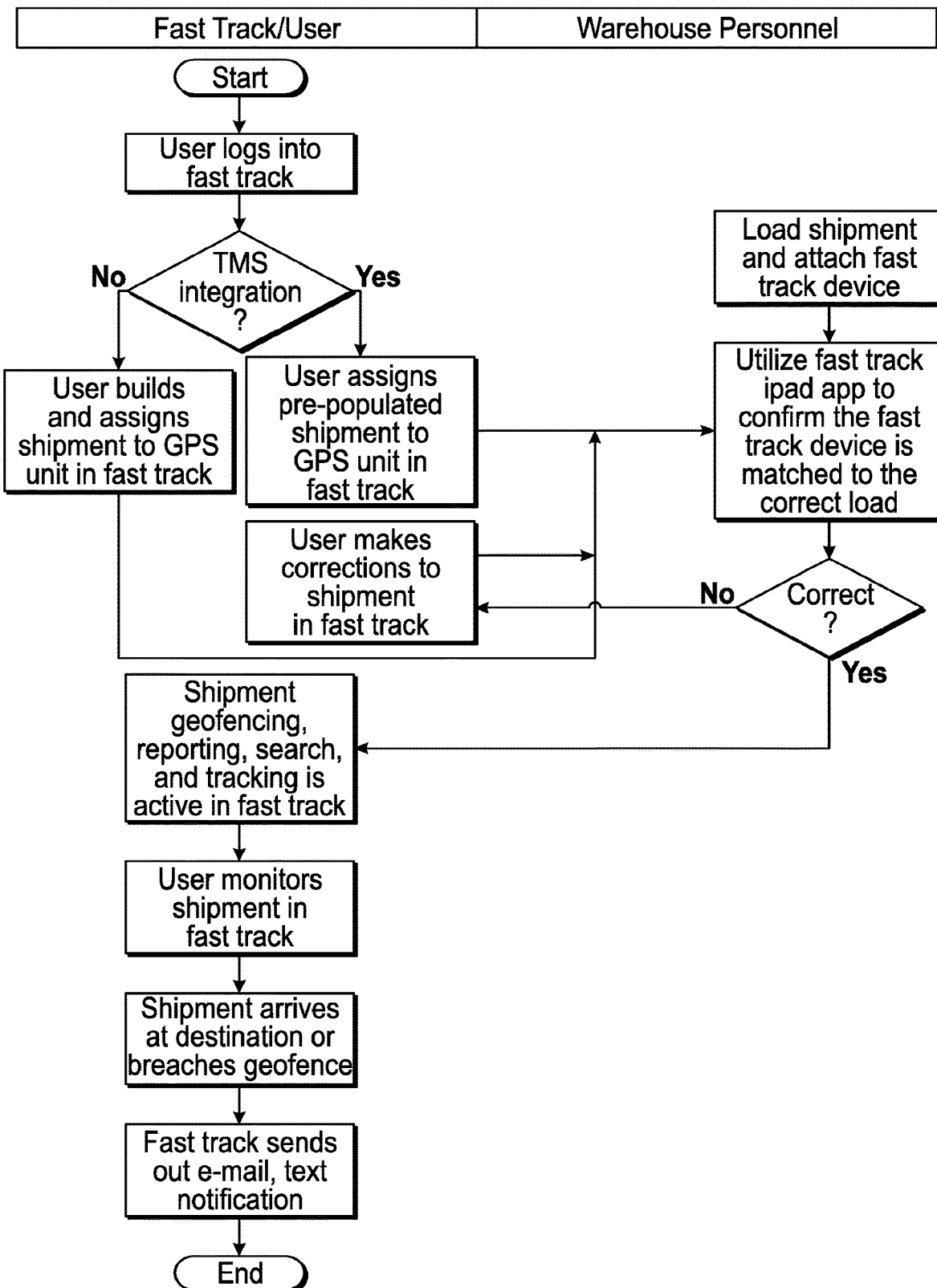
FIG. 24 is a flow chart showing an automated freight tracking system, according to an exemplary embodiment of the present invention.

FIG. 24 is a flow chart showing an automated freight load tracking system ("Fast Track system") using tracking device ("Fast Track device") (160). Fast Track system described in FIG. 23 may be implemented using the apparatuses, systems and methods described herein, including various embodiments thereof.

The Fast Track system using the Fast Track device (160) includes the following steps. A user first logs onto the Fast Track system. In an exemplary embodiment, user may log into the system via a Fast Track iPad software application/app. In other embodiments, software or apps of any other device, including any smart phone or computer, may be used. If a pre-existing TMS exists for the user's login information, the user assigns a pre-populated shipment to a GPS unit in the Fast Track device (160). If no such TMS integration exists, the user builds and assigns a shipment to the GPS unit in the Fast Track device (160). At this time, warehouse personnel at a facility load the shipment to a trailer and/or container and securely attach/lock the Fast Track device (including housing (250, 600, 601)) (160) thereto. Particularly, the personnel may secure the device (160) to the trailer and/or container using a seal (for example, a bolt seal and/or wire/tie seal) such that the device (160) cannot be accessed without breaking the seal.

At this point, the user may use the Fast Track system to confirm that the Fast Track device (160) is matched to the correct load/shipment designated by user. If the Fast Track device (160) is not matched to the correct load, the user makes corrections to the assigned shipment using the Fast Track system. If the device (160) is matched to the correct load, the Fast Track system initiates freight load tracking and activates its features, including but not limited to shipment geofencing, advanced reporting, smart searching, and/or tracking of the load/shipment. The user then monitors the shipment via the Fast Track system. If the shipment breaches a geofence, the Fast Track system sends out an instant email and/or SMS text message notification regarding this breach. Instant email and/or text message updates are also sent once the shipment arrives at a designated destination. Otherwise, email and/or text updates are sent hourly. In other embodiments, updates may be customized as needed to be sent at any other interval designated by user.

Although disclosed as being sent via SMS, text messages, updates and/or notifications may also be sent via a mobile data connection. Fast Track system may transmit and receive http communications between the device (160) and server via the mobile data connection. Transmitted information includes but is not limited to device information, battery life, speed, direction, GPS coordinates, and/or time. Information received includes but is not limited to coordinates for destinations and geofences. In embodiments, logic is put in place to preserve battery life of the tracking device (160). For example, GSM communications (215) located in tracking device (160) may be put into sleep mode between updates. Further, GSM communications (215) may be put into sleep mode while the trailer/container/vehicle/truck is stationary.

While the embodiments are described with reference to various implementations and exploitations, it will be understood that these embodiments are illustrative and that the scope of the inventions is not limited to them. Many variations, modifications, additions, and improvements are possible. Further still, any steps described herein may be carried out in any desired order, and any desired steps may be added or deleted.

What is claimed is:

1. A system for sealing and tracking a container, comprising:
   a removable tracking device; and
   a seal, a processor that is configured to determine a presence or absence of a GSM signal and to transmit information via a GSM or satellite communication channel based on the determination, wherein the tracking device is configured to transmit a location of the container continuously via a wireless communication channel, and wherein the tracking device is configured to be securely attached to the seal and to the container such that the container cannot be accessed without breaking the seal.

2. The system of claim 1, further comprising:
an accelerometer configured to measure acceleration of the container; and
a GSM communication device configured to provide acceleration and location data to a remote computer.

3. The system of claim 2, further comprising a power supply that includes a battery and/or a solar panel.

4. The system of claim 2, further comprising a sensor that monitors breakage of the seal, the sensor connected to the GSM communication device.

5. The system of claim 4, wherein the sensor that monitors breakage of the seal is a conductance based sensor.

6. The system of claim 2, further comprising a satellite communication device configured to forward the acceleration and location data of the container to a distant computer if GSM communication is not possible.

7. The system of claim 1, further comprising:
a universal connection configured to connect to multiple different types of seals and containers.

8. The system of claim 1, wherein the tracking device includes temperature and vibration sensors.

9. The system of claim 1, wherein the tracking device is configured to transmit tracking data via a satellite and/or an internet connection.

10. The system of claim 1, wherein the tracking device further comprises a memory that is configured to store a bill of lading for a shipment in digital form.

11. The system of claim 1, wherein the tracking device is further configured to transmit tracking information in an encrypted form.

12. A tracking device configured to track movement of a container, the tracking device comprising:
a housing that encloses a GPS tracking device;
a processor that is configured to determine a presence or absence of a GSM signal and to transmit information via a GSM or satellite communication channel based on the determination; and
a rigid connector integrated with the housing and configured to be securely attached to the container and a seal such that the container cannot be opened without breaking the seal,
wherein the tracking device is configured to be attached with a rigid connection that prevents relative motion between the tracking device and the container during transit.

13. The tracking device of claim 12, further comprising:
an accelerometer configured to measure acceleration of the container;
a GSM communication device configured to provide acceleration and location data to a remote computer; and
a power supply.

14. The tracking device of claim 13, wherein the power supply includes a battery and/or a solar panel.

15. The tracking device of claim 13, further comprising a sensor that monitors breakage of the seal, the sensor connected to the GSM communication device.

16. The tracking device of claim 15, wherein the sensor that monitors breakage of the seal is a conductance based sensor.

17. The tracking device of claim 12, wherein the tracking device is configured to transmit tracking data via a satellite and/or an internet connection.

18. The tracking device of claim 12, wherein the tracking device is further configured to transmit tracking information in an encrypted form.

19. A method of broker trucking, comprising:
sealing a container with a seal that is securely attached to a tracking device such that neither the container nor the tracking device can be accessed without breaking the seal;
determining, via the tracking device, a presence or absence of a GSM signal; and
transmitting, via the tracking device, a location of the container via a wireless communication channel during transit of the container, wherein tracking information is transmitted via a GSM or satellite communication channel based on the determination,
wherein the tracking device is attached to the container with a rigid connection that stabilizes and protects the tracking device during transit of the container and that prevents relative motion between the tracking device and the container.

* * * * *